United States Patent
Connor

(10) Patent No.: US 11,950,881 B2
(45) Date of Patent: Apr. 9, 2024

(54) SMART BRA FOR OPTICAL SCANNING OF BREAST TISSUE TO DETECT ABNORMAL TISSUE WITH SELECTIVELY-EXPANDABLE COMPONENTS TO REDUCE AIR GAPS

(71) Applicant: Robert A. Connor, St. Paul, MN (US)

(72) Inventor: Robert A. Connor, St. Paul, MN (US)

(73) Assignee: Holovsions LLC, Ham Lake, MN (US)

( * ) Notice: Subject to any disclaimer, the term of this patent is extended or adjusted under 35 U.S.C. 154(b) by 0 days.

(21) Appl. No.: 17/897,182

(22) Filed: Aug. 28, 2022

(65) Prior Publication Data

US 2022/0409060 A1 Dec. 29, 2022

Related U.S. Application Data

(63) Continuation-in-part of application No. 16/933,138, filed on Jul. 20, 2020, now abandoned.

(60) Provisional application No. 62/879,485, filed on Jul. 28, 2019.

(51) Int. Cl.
*A61B 5/00* (2006.01)
*A41C 3/00* (2006.01)
*A41C 3/10* (2006.01)

(52) U.S. Cl.
CPC .......... *A61B 5/0091* (2013.01); *A41C 3/0064* (2013.01); *A61B 5/0064* (2013.01); *A61B 5/6804* (2013.01); *A61B 5/6844* (2013.01); *A41C 3/0028* (2013.01); *A41C 3/0035* (2013.01); *A41C 3/105* (2013.01)

(58) Field of Classification Search
None
See application file for complete search history.

(56) References Cited

U.S. PATENT DOCUMENTS

| | | |
|---|---|---|
| 5,876,339 A | 3/1999 | Lemire |
| 5,999,836 A | 12/1999 | Nelson et al. |
| 6,081,322 A | 6/2000 | Barbour |
| 6,240,309 B1 | 5/2001 | Yamashita et al. |
| 6,345,194 B1 | 2/2002 | Nelson et al. |
| 6,571,116 B2 | 5/2003 | Wake et al. |
| 6,640,133 B2 | 10/2003 | Yamashita et al. |
| 6,738,658 B2 | 5/2004 | Wake et al. |
| RE38,800 E | 9/2005 | Barbour |
| 7,142,906 B2 | 11/2006 | Yamashita et al. |
| 7,809,422 B2 | 10/2010 | Corbeil et al. |
| 7,904,139 B2 | 3/2011 | Chance |
| 8,027,711 B2 | 9/2011 | Jones et al. |
| 8,224,426 B2 | 7/2012 | Lilge et al. |
| 8,565,862 B2 | 10/2013 | Intes et al. |

(Continued)

OTHER PUBLICATIONS

Ahmed et al., 2021, "Differential Optical Absorption Spectroscopy-Based Refractive Index Sensor for Cancer Cell Detection," Optical Review, 28, 134-143.

(Continued)

*Primary Examiner* — Pascal M Bui Pho
*Assistant Examiner* — Michael S Kellogg

(57) ABSTRACT

This invention is a smart bra for optical scanning of breast tissue which has light emitters which transmit light into breast tissue, light receivers which receive the light after it has been transmitted through the breast tissue, and expandable components which selectively move light emitters and/or receivers closer to the surface of a breast where there are air gaps.

7 Claims, 7 Drawing Sheets

(56) References Cited

U.S. PATENT DOCUMENTS

Figure 1:
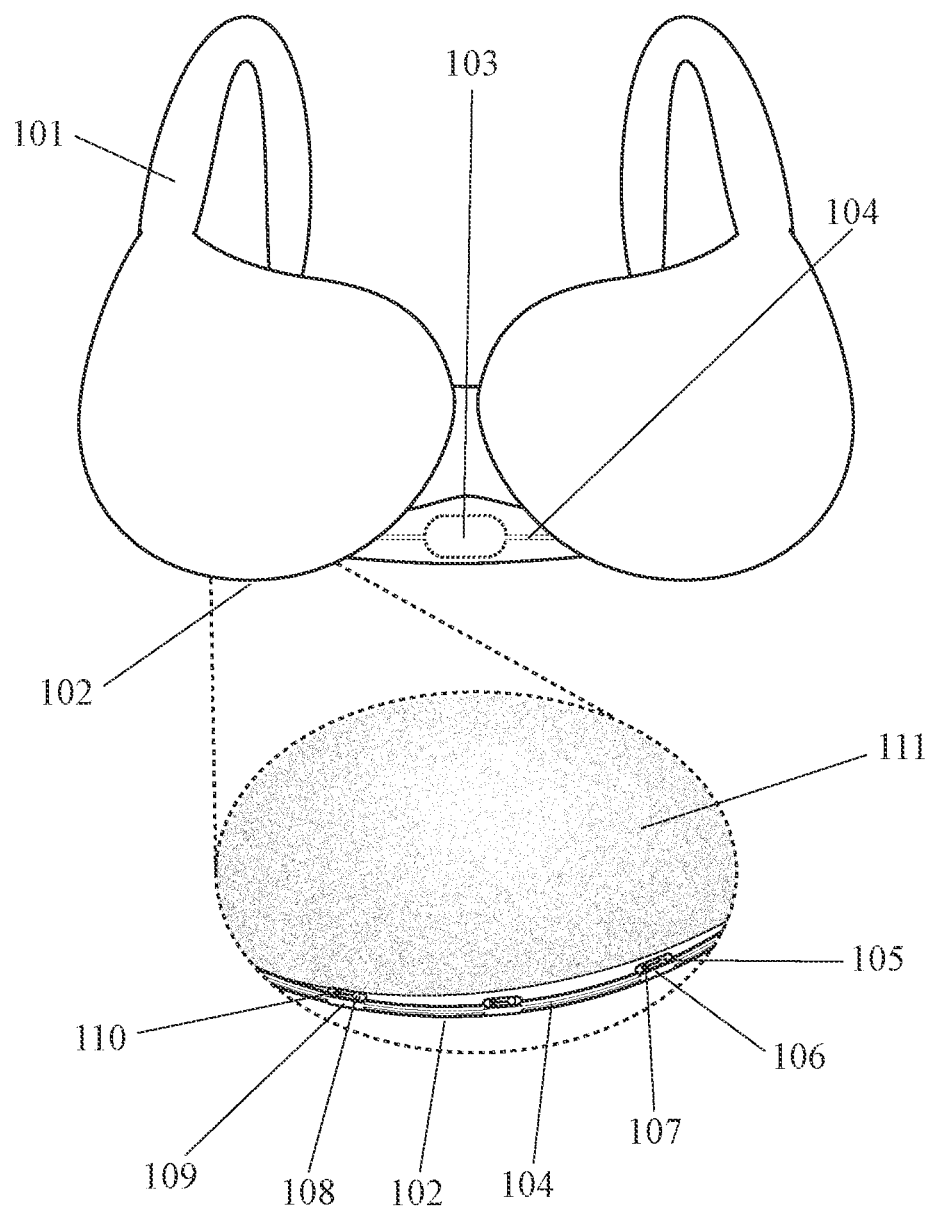

| | | | |
|---|---|---|---|
| 9,314,218 B2 | 4/2016 | Stearns et al. | |
| 9,495,516 B2 | 11/2016 | Hielscher et al. | |
| 9,513,276 B2 | 12/2016 | Tearney et al. | |
| 9,597,046 B2 | 3/2017 | Goossen et al. | |
| 9,724,489 B2 | 8/2017 | Barbour et al. | |
| 9,770,220 B2 | 9/2017 | Stearns et al. | |
| 9,993,159 B2 | 6/2018 | Islam | |
| 10,111,594 B2 | 10/2018 | Hielscher et al. | |
| 10,130,318 B2 | 11/2018 | Stearns et al. | |
| 10,178,967 B2 | 1/2019 | Hielscher et al. | |
| 10,200,655 B2 | 2/2019 | Kim et al. | |
| 10,215,636 B2 | 2/2019 | Fujii et al. | |
| 10,376,150 B2 | 8/2019 | Hielscher et al. | |
| 10,506,181 B2 | 12/2019 | Delgado et al. | |
| 10,653,346 B2 | 5/2020 | Zarandi et al. | |
| 2002/0045833 A1 | 4/2002 | Wake et al. | |
| 2004/0092826 A1 | 5/2004 | Corbeil et al. | |
| 2005/0043596 A1 | 2/2005 | Chance | |
| 2006/0058683 A1 | 3/2006 | Chance | |
| 2006/0173352 A1 | 8/2006 | Lilge et al. | |
| 2007/0287897 A1 | 12/2007 | Faris | |
| 2009/0005692 A1 | 1/2009 | Intes et al. | |
| 2010/0292569 A1 | 11/2010 | Hielscher et al. | |
| 2013/0260639 A1* | 10/2013 | Lin | A41C 3/105 450/38 |
| 2013/0289394 A1 | 10/2013 | Hielscher et al. | |
| 2013/0338496 A1 | 12/2013 | Hielscher et al. | |
| 2014/0088415 A1 | 3/2014 | Hielscher et al. | |
| 2014/0236003 A1 | 8/2014 | Hielscher et al. | |
| 2014/0236021 A1 | 8/2014 | Islam | |
| 2014/0243681 A1 | 8/2014 | Hielscher et al. | |
| 2014/0330116 A1 | 11/2014 | Hielscher et al. | |
| 2015/0119665 A1 | 4/2015 | Barbour et al. | |
| 2015/0182121 A1* | 7/2015 | Barbour | A61B 5/0073 600/425 |
| 2015/0223697 A1 | 8/2015 | Hielscher et al. | |
| 2015/0286785 A1 | 10/2015 | Hielscher et al. | |
| 2016/0066811 A1 | 3/2016 | Mohamadi | |
| 2017/0007187 A1 | 1/2017 | Breneisen et al. | |
| 2017/0027480 A1 | 2/2017 | Hielscher et al. | |
| 2017/0105625 A1 | 4/2017 | Eum | |
| 2017/0209083 A1 | 7/2017 | Zarandi et al. | |
| 2018/0070891 A1 | 3/2018 | Jepsen | |
| 2018/0289264 A1 | 10/2018 | Islam | |
| 2018/0335753 A1 | 11/2018 | Jepsen et al. | |
| 2019/0072897 A1 | 3/2019 | Jepsen et al. | |
| 2019/0150526 A1* | 5/2019 | Lehna | A41C 3/06 |
| 2019/0239751 A1 | 8/2019 | Hielscher et al. | |
| 2019/0282134 A1 | 9/2019 | Hielscher et al. | |
| 2020/0116630 A1 | 4/2020 | Zhu | |
| 2021/0038083 A1 | 2/2021 | Islam | |

OTHER PUBLICATIONS

Altoe et al., 2019, "Diffuse Optical Tomography of the Breast: A Potential Modifiable Biomarker of Breast Cancer Risk with Neoadjuvant Chemotherapy," Biomedical Optics Express, Aug. 1, 2019, 10(8), 4305-4315.

Altoe et al., 2021, "Effects of Neoadjuvant Chemotherapy on the Contralateral Non-Tumor-Bearing Breast Assessed by Diffuse Optical Tomography," Breast Cancer Research, 2021, 23, 16.

Anderson et al., 2017, "Optical Mammography in Patients with Breast Cancer Undergoing Neoadjuvant Chemotherapy: Individual Clinical Response Index," Academic Radiology, Oct. 2017, 24(10), 1240-1255.

Angelo et al., 2018, "Review of Structured Light in Diffuse Optical Imaging, " Journal of Biomedical Optics, Sep. 14, 2018, 24(7), 071602.

Applegate et al., 2018, "Multi-Distance Diffuse Optical Spectroscopy with a Single Optode via Hypotrochoidal Scanning," Optics Letters, 2018, 43, 747-750.

Chae et al., 2020, "Development of Digital Breast Tomosynthesis and Diffuse Optical Tomography Fusion Imaging for Breast Cancer Detection," Scientific Reports, 10, 13127 (2020).

Chitnis et al., 2016, "Towards a Wearable Near Infrared Spectroscopic Probe for Monitoring Concentrations of Multiple Chromophores in Biological Tissue in Vivo," Review of Scientific Instruments. Jun. 2016, 87(6), 065112.

Cochran et al., 2019, "Hybrid Time-Domain and Continuous-Wave Diffuse Optical Tomography Instrument with Concurrent, Clinical Magnetic Resonance Imaging for Breast Cancer Imaging," Journal of Biomedical Optics, Jan. 2019, 24(5), 1-11.

Durduran et al., 2010, 2010, "Diffuse Optics for Tissue Monitoring and Tomography," Reports on Progress in Physics, 2010, 73(7), 076701.

Fakayode et al., 2020, "Molecular (Raman, NIR, and FTIR) Spectroscopy and Multivariate Analysis in Consumable Products Analysis," Applied Spectroscopy Reviews, 55:8, 647-723.

Fantini et al., 2005, "Optical Spectroscopy and Imaging of Tissues," NSF Award # 0093840, Jun. 1, 2001.

Fantini et al., 2012, "Near-Infrared Optical Mammography for Breast Cancer Detection with I ntrinsic Contrast," Annals of Biomedical Engineering, Feb. 2012, 40(2), 398-407.

Farmani et al., 2020, "Optical Nanosensors for Cancer and Virus Detections," Micro and Nano Technologies, Nanosensors for Smart Cities, Chapter 25, Han et al. editors, Elsevier, 2020, 419-432, ISBN 9780128198704.

Flexman et al., 2008, "The Design and Characterization of a Digital Optical Breast Cancer Imaging System," 30th Annual International Conference of the IEEE Engineering in Medicine and Biology Society, 2008, 3735-3738.

Ghijsen et al., 2018, "Quantitative Real-Time Optical Imaging of the Tissue Metabolic Rate of Oxygen Consumption," Journal of Biomedical Optics, Mar. 24, 2018, 23(3), 036013.

Grosenick et al., 2016, "Review of Optical Breast Imaging and Spectroscopy," Journal of Biomedical Optics, Sep. 2016, 21(9), 091311.

Gunther et al., 2018, "Dynamic Diffuse Optical Tomography for Monitoring Neoadjuvant Chemotherapy in Patients with Breast Cancer," Radiology, Jun. 2018; 287(3): 778-786.

Hoi et al., 2018, "Non-Contact Dynamic Diffuse Optical Tomography Imaging System for Evaluating Lower Extremity Vasculature," Biomedical Optics Express, 2018, 9, 5597-5614.

Imamura et al., 2018, "In Vivo Optical Imaging of Cancer Cell Function and Tumor Microenvironment," Cancer Science, 2018, 109, 912-918.

Intes et al., 2004, "Time-Domain Optical Mammography Softscan: Initial Results on Detection and Characterization of Breast Tumors," Proceedings SPIE 5578, Photonics North 2004: Photonic Applications in Astronomy, Biomedicine, Imaging, Materials Processing, and Education, Dec. 9, 2004.

Jeong et al., 2020, "Emerging Advanced Metasurfaces: Alternatives to Conventional Bulk Optical Devices," Microelectronic Engineering, 2020, vol. 220, 111146, ISSN 0167-9317.

Joshi et al., 2018, "Targeted Optical Imaging Agents in Cancer: Focus on Clinical Applications," Contrast Media and Molecular Imaging, Aug. 27, 2018.

Jung et al., 2015, "Non-Contact Deep Tissue Imaging using a Hand-Held Near-infrared Optical Scanner," Journal of Medical Diagnostic Methods, Mar. 24, 2015, 4(2), 1-10.

Khan, 2013, "Image Reconstruction in Diffuse Optical Tomography with Sparsity Constraints," NSF Award, 2009.

Kim et al., 2016, "US-Localized Diffuse Optical Tomography in Breast Cancer: Comparison with Pharmacokinetic Parameters of DCE-MRI and With Pathologic Biomarkers," BMC Cancer, Feb. 1, 2016, 16:50.

Koetse et al., 2007, "Optical Sensor Array Platform Based on Polymer Electronic Devices," Proceedings SPIE 6739, Electro-Optical Remote Sensing, Detection, and Photonic Technologies and Their Applications, 67391D, Nov. 7, 2007.

Koomson, 2019, "A Noninvasive Biological Research Tool for Measurement of Tissue and Cerebral Oxygenation," NSF Award # 1919038, Jul. 15, 2019.

(56) References Cited

OTHER PUBLICATIONS

Krishnamurthy, 2018, "Using Near-Infrared Spectroscopy to Study Static and Dynamic Hemoglobin Contrast Associated with Breast Cancer," Tufts University, Dissertation, 2018.
Leo et al., 2017, "Optical Imaging of the Breast: Basic Principles and Clinical Applications," American Journal of Roentgenology, 2017, 209:1, 230-238.
Li et al., 2018, "Sensitive and Wearable Optical Microfiber Sensor for Human Health Monitoring," Advanced Materials Technologies, 2018, 3, 1800296.
Liu et al., 2018, "Diffuse Optical Spectroscopy for Monitoring the Responses of Patients with Breast Cancer to Neoadjuvant Chemotherapy: A Meta-Analysis," Medicine, 2018, 97(41), 12683.
Liu et al., 2020, "Recent Progress in Flexible Wearable Sensors for Vital Sign Monitoring," Sensors, 2020, 20(14), 4009.
Liu et al., 2021, "Simultaneous Measurements of Tissue Blood Flow and Oxygenation Using a Wearable Fiber-Free Optical Sensor," Journal of Biomedical Optics, Jan. 29, 2021, 26(1), 012705.
Lutzweiler et al., 2013, "Optoacoustic Imaging and Tomography: Reconstruction Approaches and Outstanding Challenges in Image Performance and Quantification," Sensors, 2013, 13(3), 7345-7384.
Ma et al., 2020b, "Fiber-Free Parallel-Plane Continuous Wave Breast Diffuse Optical Tomography System," SPIE 11229, Advanced Biomedical and Clinical Diagnostic and Surgical Guidance Systems XVIII. Proceedings, 112290L, Feb. 21, 2020.
Mabou et al., 2018, "Breast Cancer Detection Using Infrared Thermal Imaging and a Deep Learning Model," Sensors, 2018, 18(9), 2799.
Moreno et al., 2019, "Evaluation on Phantoms of the Feasibility of a Smart Bra to Detect Breast Cancer in Young Adults," Sensors, 2019, 19(24), 5491.
Nguyen et al., 2020, "Preliminary Development of Optical Computed Tomography (Optical CT) Scanner Using Transillumination Imaging NAD," Conference: International Symposium on Applied Science 2019, Hochiminh City, Vietnam, May 14, 2020.
Pan et al., 2020, "A Multifunctional Skin-Like Wearable Optical Sensor Based on an Optical Micro-/Nanofibre," Nanoscale, 2020, Issue 33.
Park et al., 2013, "Multispectral Imaging Using Polydimethylsiloxane (PDMS) Embedded Vertical Silicon Nanowires," OSA Technical Digest (online) (Optical Society of America, 2013), paper CTu3O.1.
Park et al., 2015, "Vertically Stacked Photodetector Devices Containing Silicon Nanowires with Engineered Absorption Spectra," ACS Photonics, Mar. 16, 2015, 2(4), 544-549.
Perumal et al., 2019, "Near Infra-Red Polymeric Nanoparticle Based Optical Imaging in Cancer Diagnosis," Journal of Photochemistry and Photobiology, Biology, 2019, vol. 199, 111630, ISSN 1011-1344.
Pinti et al., 2018, "A Review on the Use of Wearable Functional Near-Infrared Spectroscopy in Naturalistic Environments," Japanese Psychology Research, Oct. 2018, 60(4), 347-373.
Qiu, 2018, "Implantable Ultra-Low Power VO2 MEMS Scanner Based Surface-Enhanced Raman Spectroscope for Wide-Field Tumor Imaging in Free Moving Small Animals," NSF Award, 2018.
Rahman et al., 2016, "Electromagnetic Performances Analysis of an Ultra-Wideband and Flexible Material Antenna in Microwave Breast Imaging: To Implement a Wearable Medical Bra," Scientific Reports, 2016, vol. 6, 38906.
Ray et al., 2017, "A Systematic Review of Wearable Systems for Cancer Detection: Current State and Challenges," Journal of Medical Systems, Oct. 2, 2017, 41(11), 180.
Robbins et al., 2021, "Two-Layer Spatial Frequency Domain Imaging of Compression-Induced Hemodynamic Changes in Breast Tissue," Journal of Biomedical Optics, May 24, 2021, 26(5), 056005.
Roblyer et al., 2020b, "Tracking Breast Cancer Therapies with Handheld and Wearable Diffuse Optics," Biophotonics Congress: Biomedical Optics 2020 (Translational, Microscopy, OCT, OTS, Brain), OSA Technical Digest (Optical Society of America, 2020), paper TM4B.1.
Shokoufi et al., 2017, "Novel Handheld Diffuse Optical Spectroscopy Probe for Breast Cancer Assessment: Clinical Study," Journal of Biomedical Science, 6(5), 34.
Soliman et al., 2010, "Functional Imaging Using Diffuse Optical Spectroscopy of Neoadjuvant Chemotherapy Response in Women with Locally Advanced Breast Cancer," Clinical Cancer Research, Apr. 20, 2010, 15, 2605-2614.
Spink et al., 2020, "High Optode-Density Wearable Probe for Monitoring Breast Tumor Dynamics During Neoadjuvant Chemotherapy," Biophotonics Congress: Biomedical Optics 2020 (Translational, Microscopy, OCT, OTS, Brain), OSA Technical Digest, paper TTu1B.2.
Spink et al., 2021, "High Optode-Density Wearable Diffuse Optical Probe for Monitoring Paced Breathing Hemodynamics in Breast Tissue," Journal of Biomedical Optics, Jun. 2, 2021, 26(6), 062708.
Tank et al., 2020, "Diffuse Optical Spectroscopic Imaging Reveals Distinct Early Breast Tumor Hemodynamic Responses to Metronomic and Maximum Tolerated Dose Regimens," Breast Cancer Research, 2020, 22, 29.
Teng et al., 2017, "Wearable Near-Infrared Optical Probe for Continuous Monitoring During Breast Cancer Neoadjuvant Chemotherapy Infusions," Journal of Biomedical Optics, 22(1), 14001.
Teng, 2018, "A Wearable Near-Infrared Diffuse Optical System for Monitoring in Vivo Breast Tumor Hemodynamics During Chemotherapy Infusions," Boston University, Dissertation, 2018.
Tromberg et al., 2016, "ACRIN 6691 Investigators. Predicting Responses to Neoadjuvant Chemotherapy in Breast Cancer," Cancer Research, Aug. 15, 2016, 76(20), 5933-5944.
Uddin et al., 2020a, "Optimal Breast Cancer Diagnostic Strategy Using Combined Ultrasound and Diffuse Optical Tomography," Biomedical Optics Express, 11(5), 2722-2737.
Upputuri, 2019, "Photoacoustic Imaging in the Second Near-Infrared Window: A Review," Journal of Biomedical Optics, Apr. 9, 2019, 24(4), 040901.
Vavadi et al., 2018, "Compact Ultrasound-Guided Diffuse Optical Tomography System for Breast Cancer Imaging," Journal of Biomedical Optics, 2018, 24(2), 1-9.
Wang et al., 2020, "Development of a Prototype of a Wearable Flexible Electro-Optical Imaging System for the Breast," Biophotonics Congress: Biomedical Optics 2020 (Translational, Microscopy, OCT, OTS, Brain), OSA Technical Digest, paper TM4B.4.
Yu et al., 2010, "Near-Infrared, Broad-Band Spectral Imaging of the Human Breast for Quantitative Oximetry: Applications to Healthy and Cancerous Breasts," Journal of Innovative Optical Health Sciences, Oct. 2010, 03(4):267-277.
Yuan et al., 2014, "Light-Emitting Diode-Based Multiwavelength Diffuse Optical Tomography System Guided by Ultrasound," Journal of Biomedical Optics, Dec. 4, 2014, 19(12) 126003.
Zhang et al., 2020, "Efficacy of Shear-Wave Elastography Versus Dynamic Optical Breast Imaging for Predicting the Pathological Response to Neoadjuvant Chemotherapy in Breast Cancer," European Journal of Radiology, 2020, 129, 109098.
Zhu et al., 2020, "A Review of Optical Breast Imaging: Multi-Modality Systems for Breast Cancer Diagnosis," European Journal of Radiology, Aug. 2020, 129:109067.
Zhu et al., 2021, "Early Assessment Window for Predicting Breast Cancer Neoadjuvant Therapy Using Biomarkers, Ultrasound, and Diffuse Optical Tomography," Breast Cancer Research and Treatment, 2021.

\* cited by examiner

SMART BRA FOR OPTICAL SCANNING OF BREAST TISSUE TO DETECT ABNORMAL TISSUE WITH SELECTIVELY-EXPANDABLE COMPONENTS TO REDUCE AIR GAPS

CROSS-REFERENCE TO RELATED APPLICATIONS

This application is a continuation-in-part of U.S. application Ser. No. 16/933,138 filed on 2020 Jul. 20 which, in turn, claimed the priority benefit of U.S. provisional application 62/879,485 filed on 2019 Jul. 28. The entire contents of these related applications are incorporated herein by reference

FEDERALLY SPONSORED RESEARCH

Not Applicable

SEQUENCE LISTING OR PROGRAM

Not Applicable

BACKGROUND

Field of Invention

This invention relates to wearable medical devices for imaging and diagnosis.

Introduction

Breast cancer is the most common form of cancer in women and a leading cause of death. Breast imaging can serve a critical role in the early diagnosis and treatment of breast cancer. However, there are limitations to frequent use of the current breast imaging modalities. Current modalities of breast imaging and/or abnormal tissue detection include: x-ray mammography (most common), Magnetic Resonance Imaging (MRI), and ultrasonography. Limitations of x-ray mammography include exposure to ionizing radiation, lower accuracy for younger individuals and those with dense breast tissue, uncomfortable compression of the breast, relatively high false positive rate, and two-dimensional images. Limitations of Magnetic Resonance Imaging (MRI) include relatively low specificity, long exam times, and high cost. Limitations of ultrasound imaging include difficulty visualizing microcalcifications and strong dependence on examiner interpretation. General limitations of current modalities include required access to specialized facilities, examination time required, embarrassment and/or cultural barriers. There remains a need for a new breast imaging modality which can be used frequently and safely for breast imaging and tissue analysis.

During recent years, there has been increased investigation of the possibilities of optical breast imaging using safe non-ionizing radiation such as visible, ultraviolet, infrared, and near-infrared light energy. However, thus far there have been limitations to optical breast imaging. For example, with stationary devices, there can be air gaps between optical sensors and the surface of a breast which reduce scanning accuracy. Also, with handheld optical imaging devices, it can be difficult to accurately measure absolute tissue locations to track changes over time and to get a comprehensive image of the complete breast.

Review of the Relevant Art

In the patent literature, U.S. patent application 20050043596 (Chance, Feb. 24, 2005, "Optical Examination Device, System and Method") discloses a brush-form optical coupler with freely extending fiber end portions, sized and positioned to make optical contact with a subject, examination, and monitoring systems utilizing one or more of such couplers. U.S. patent application 20060058683 (Chance, Mar. 16, 2006, "Optical Examination of Biological Tissue Using Non-Contact Irradiation and Detection") and U.S. Pat. No. 7,904,139 (Chance, Mar. 8, 2011, "Optical Examination of Biological Tissue Using Non-Contact Irradiation and Detection") disclose an optical system for examination of biological tissue which includes a light source, a light detector, optics and electronics.

U.S. Pat. No. 6,081,322 (Barbour, Jun. 27, 2000, "NIR Clinical Opti-Scan System") and RE38800 (Barbour, Sep. 20, 2005, "NIR Clinical Opti-Scan System") disclose three-dimensional optical imaging techniques for the detection and three-dimensional imaging of absorbing and/or scattering structures in complex random media, such as human body tissue, by detecting scattered light. U.S. patent application 20150182121 (Barbour, Jul. 2, 2015, "Low-Cost Screening System for Breast Cancer Detection") discloses a portable and wearable tumor detector including a brassier and devices for optical tomography. U.S. patent application publication 20150119665 (Barbour et al., Apr. 30, 2015, "Self-Referencing Optical Measurement for Breast Cancer Detection") and U.S. Pat. No. 9,724,489 (Barbour et al., Aug. 8, 2017, "Self-Referencing Optical Measurement for Breast Cancer Detection") disclose obtaining optical data from a pair of breasts, employing a simultaneous bilateral referencing protocol, and employing a self-referencing data analysis method.

U.S. patent applications 20100292569 (Hielscher et al., Nov. 18, 2010, "Systems and Methods for Dynamic Imaging of Tissue Using Digital Optical Tomography") and 20150223697 (Hielscher et al., Aug. 13, 2015, "Systems and Methods for Dynamic Imaging of Tissue Using Digital Optical Tomography") disclose methods for imaging tissue using diffuse optical tomography including directing a amplitude modulated optical signals from optical signal sources. U.S. patent application 20140330116 (Hielscher et al., Nov. 6, 2014, "Systems and Methods for Simultaneous Multi-Directional Imaging for Capturing Tomographic Data") discloses devices, systems, and method for tomographic imaging in which light transmitted and backscattered surface light is imaged by an optical system that minimizes reflection back to the target object. U.S. patent applications 20130289394 (Hielscher et al., Oct. 31, 2013, "Dynamic Optical Tomographic Imaging Devices Methods and Systems"), 20170027480 (Hielscher et al., Feb. 2, 2017, "Dynamic Optical Tomographic Imaging Devices Methods and Systems"), and 20190282134 (Hielscher et al., Sep. 19, 2019, "Dynamic Optical Tomographic Imaging Devices Methods and Systems"), and U.S. Pat. No. 10,178,967 (Hielscher et al., Jan. 15, 2019, "Dynamic Optical Tomographic Imaging Devices Methods and Systems") disclose an optical tomographic systems for acquiring and displaying dynamic data representing changes in a target tissue sample to external provocation. U.S. patent applications 20130338496 (Hielscher et al., Dec. 19, 2013, "Medical Imaging Devices, Methods, and Systems") and 20140088415 (Hielscher et al., Mar. 27, 2014, "Medical Imaging Devices, Methods, and Systems") disclose devices, methods, and systems for generating optical tomographic data including volumetric and surface geometric data.

U.S. patent application publication 20140236003 (Hielscher et al., Aug. 21, 2014, "Interfacing Systems, Devices, and Methods for Optical Imaging") discloses an imaging interface with a plurality of concentric rings for diffuse optical tomography of breast tissue. U.S. patent applications 20140243681 (Hielscher et al., Aug. 28, 2014, "Compact Optical Imaging Devices, Systems, and Methods") and 20190239751 (Hielscher et al., Aug. 8, 2019, "Compact Optical Imaging Devices, Systems, and Methods"), and U.S. Pat. No. 10,111,594 (Hielscher et al., Oct. 30, 2018, "Compact Optical Imaging Devices, Systems, and Methods") disclose a handheld optical imaging system with a plurality of detectors. U.S. patent application 20150286785 (Hielscher et al., Oct. 8, 2015, "Systems, Methods, and Devices for Image Reconstruction Using Combined PDE-Constrained and Simplified Spherical Harmonics Algorithm") and U.S. Pat. No. 9,495,516 (Hielscher et al., Nov. 15, 2016, "Systems, Methods, and Devices for Image Reconstruction Using Combined PDE-Constrained and Simplified Spherical Harmonics Algorithm") disclose systems, methods, and devices for image reconstruction using combined PDE-constrained and simplified spherical harmonics (SPN) algorithms. U.S. Pat. No. 10,376,150 (Hielscher et al., Aug. 13, 2019, "Interfacing Systems, Devices, and Methods for Optical Imaging") discloses an imaging interface for diffuse optical tomography of breast with a plurality of concentric rings.

U.S. patent application publication 20140236021 (Islam, Aug. 21, 2014, "Near-Infrared Super-Continuum Lasers for Early Detection of Breast and Other Cancers") and U.S. Pat. No. 9,993,159 (Islam, Jun. 12, 2018, "Near-Infrared Super-Continuum Lasers for Early Detection of Breast and Other Cancers") disclose a system and method using near-infrared or short-wave infrared light sources for early detection and monitoring of breast cancer. U.S. patent application publication 20180289264 (Islam, Oct. 11, 2018, "High Signal-to-Noise Ratio Light Spectroscopy of Tissue") discloses a diagnostic system which delivers an optical beam to a nonlinear element that broadens a spectrum of the first optical beam to at least 10 nanometers through a nonlinear effect in the nonlinear element. U.S. patent application 20210038083 (Islam, Feb. 11, 2021, "Multi-Wavelength Wearable Device for Non-Invasive Blood Measurements in Tissue") discloses a system for measuring one or more physiological parameters with a wearable device that includes a light source comprising a driver and semiconductor sources that generate an output optical light.

U.S. patent application publication 20090005692 (Intes et al., Jan. 1, 2009, "Optical Imaging Method for Tissue Characterization") and U.S. Pat. No. 8,565,862 (Intes et al., Oct. 22, 2013, "Optical Imaging Method for Tissue Characterization") disclose a method for detecting and characterizing abnormalities within biological tissue by characterizing optical properties of the tissue. U.S. patent application publication 20180070891 (Jepsen, Mar. 15, 2018, "Imaging With Infrared Imaging Signals") discloses using an infrared imaging signal to image tissue. U.S. patent application publication 20180335753 (Jepsen et al., Nov. 22, 2018, "Co-Located Imaging and Display Pixel") discloses an optical transformation engine coupled between an image pixel and a display pixel. U.S. patent application publication 20190072897 (Jepsen et al., Mar. 7, 2019, "Applications of Diffuse Medium Imaging") discloses methods and an apparatus for imaging translucent materials.

U.S. Pat. No. 9,314,218 (Stearns et al., Apr. 19, 2016, "Integrated Microtomography and Optical Imaging Systems") and U.S. Pat. No. 10,130,318 (Stearns et al., Nov. 20, 2018, "Integrated Microtomography and Optical Imaging Systems") disclose an integrated microtomography and optical imaging system with a rotating table that supports an imaging object, an optical stage, and separate optical and microtomography imaging systems. U.S. Pat. No. 9,770,220 (Stearns et al., Sep. 26, 2017, "Integrated Microtomography and Optical Imaging Systems") discloses a rotating table that supports an imaging object, an optical stage, and separate optical and microtomography imaging systems. U.S. patent application 20170209083 (Zarandi et al., 2017, "Hand-Held Optical Scanner for Real-Time Imaging of Body Composition and Metabolism") and U.S. Pat. No. 10,653,346 (Zarandi et al., May 19, 2020, "Hand-Held Optical Scanner for Real-Time Imaging of Body Composition and Metabolism") disclose a handheld system for diffuse optical spectroscopic imaging of human tissue.

U.S. patent application 20060173352 (Lilge et al., 2006, "Optical Transillumination and Reflectance Spectroscopy to Quantify Disease Risk") discloses a method of illuminating tissue of a mammal with light having wavelengths covering a pre-selected spectral range, detecting light transmitted through, or reflected from, the volume of selected tissue, and obtaining a spectrum of the detected light. U.S. patent application 20200116630 (Zhu, 2020, "Compact Guided Diffuse Optical Tomography System for Imaging a Lesion Region") discloses a compact diffuse optical tomography system with laser diodes and a laser diode driver board. U.S. Pat. No. 5,876,339 (Lemire, Mar. 2, 1999, "Apparatus for Optical Breast Imaging") discloses an optical breast imager with an adjustable volume which encloses a patient's breast.

U.S. Pat. No. 5,999,836 (Nelson et al., Dec. 7, 1999, "Enhanced High Resolution Breast Imaging Device and Method Utilizing Non-Ionizing Radiation of Narrow Spectral Bandwidth") and U.S. Pat. No. 6,345,194 (Nelson et al., Feb. 5, 2002, "Enhanced High Resolution Breast Imaging Device and Method Utilizing Non-Ionizing Radiation of Narrow Spectral Bandwidth") disclose breast imaging using collimated non-ionizing radiation in the near ultraviolet, visible, infrared, and microwave regions. U.S. Pat. No. 6,240,309 (Yamashita et al., May 29, 2001, "Optical Measurement Instrument for Living Body"), U.S. Pat. No. 6,640,133 (Yamashita et al., Oct. 28, 2003, "Optical Measurement Instrument for Living Body"), and U.S. Pat. No. 7,142,906 (Yamashita et al., Nov. 28, 2006, "Optical Measurement Instrument for Living Body") disclose an optical measurement instrument which applies visible-infrared light to several positions on a patient.

U.S. patent application 20020045833 (Wake et al., Apr. 18, 2002, "Medical Optical Imaging Scanner Using Multiple Wavelength Simultaneous Data Acquisition for Breast Imaging") discloses a scanner for a medical optical imaging device with an illumination source which directs emitted light into a breast positioned below a support surface. U.S. Pat. No. 6,571,116 (Wake et al., May 27, 2003, "Medical Optical Imaging Scanner Using Multiple Wavelength Simultaneous Data Acquisition for Breast Imaging") and U.S. Pat. No. 6,738,658 (Wake et al., May 18, 2004, "Medical Optical Imaging Scanner Using Multiple Wavelength Simultaneous Data Acquisition for Breast Imaging") disclose a medical optical imaging device with an illumination source that directs emitted light into a breast positioned below a support surface.

U.S. patent application publication 20040092826 (Corbeil et al., May 13, 2004, "Method and Apparatus for Optical Imaging") and U.S. Pat. No. 7,809,422 (Corbeil et al., Oct. 5, 2010, "Method and Apparatus for Optical Imaging") disclose a platform with a cavity into which one of the person's breasts is suspended for optical imaging. U.S. patent application publication 20070287897 (Faris, Dec. 13, 2007, "Optical Vascular Function Imaging System and Method for Detection and Diagnosis of Cancerous Tumors") discloses an in-vivo optical imaging system and method of identifying unusual vasculature associated with tumors. U.S. Pat. No. 8,027,711 (Jones et al., Sep. 27, 2011, "Laser Imaging Apparatus with Variable Patient Positioning") discloses a tabletop to support a patient in front-down position and an opening to permit a breast of the patient to be vertically pendant below the tabletop.

U.S. Pat. No. 8,224,426 (Lilge et al., Jul. 17, 2012, "Optical Transillumination and Reflectance Spectroscopy to Quantify Disease Risk") discloses spectroscopic tissue volume measurements with non-ionizing radiation to detect pre-disease transformations in tissue. U.S. patent application publication 20160066811 (Mohamadi, Mar. 10, 2016, "Handheld and Portable Scanners for Millimeter Wave Mammography and Instant Mammography Imaging") discloses an array of ultra-wide band radio frequency sensors for breast imaging. U.S. Pat. No. 9,513,276 (Tearney et al., Dec. 6, 2016, "Method and Apparatus for Optical Imaging via Spectral Encoding") disclose a method, apparatus and arrangement for obtaining information associated with a sample such as a portion of an anatomical structure. U.S. patent application publication 20170007187 (Breneisen et al., Jan. 12, 2017, "Cancer Detector Using Deep Optical Scanning") discloses Deep Optical Scanning (DEOS) for the detection of breast cancer and the determination of response to therapy.

U.S. Pat. No. 9,597,046 (Goossen et al., Mar. 21, 2017, "Method and Device for Imaging Soft Body Tissue Using X-Ray Projection and Optical Tomography") discloses breast imaging using X-ray projection techniques and optical tomography techniques. U.S. patent application 20170105625 (Eum, Apr. 20, 2017, "Diagnostic Device of Optics Type for Breast") discloses an optical breast diagnostic apparatus with a hemispherical cover. U.S. Pat. No. 10,200,655 (Kim et al., Feb. 5, 2019, "Tomographic Imaging Methods, Devices, and Systems") discloses a multispectral bioluminescence optical tomography algorithm makes use of a partial differential equation (PDE) constrained approach. U.S. Pat. No. 10,215,636 (Fujii et al., Feb. 26, 2019, "Imaging Device Provided With Light Source That Emits Pulsed Light and Image Sensor") discloses an imaging device with a light source that emits pulsed light at different wavelengths. U.S. Pat. No. 10,506,181 (Delgado et al., Dec. 10, 2019, "Device for Optical Imaging") discloses the capture of an infrared image.

Turning now to non-patent literature, Chitnis et al., (2016), "Towards a Wearable Near Infrared Spectroscopic Probe for Monitoring Concentrations of Multiple Chromophores in Biological Tissue In Vivo" discloses a wearable multi-wavelength technology for functional near-infrared spectroscopy with an 8-wavelength light emitting diode (LED) source. Jung et al., (2015), "Non-Contact Deep Tissue Imaging using a Hand-Held Near-infrared Optical Scanner" discloses fiber-free non-contact near-infrared (NIR) imaging devices using wide-field detectors.

Koomson (2019), "PFI-TT: A Noninvasive Biological Research Tool for Measurement of Tissue and Cerebral Oxygenation," NSF Award, 2019 (abstract only viewed) investigates compact wearable devices with advanced NIRS capability. Liu et al., (2021), "Simultaneous Measurements of Tissue Blood Flow and Oxygenation Using a Wearable Fiber-Free Optical Sensor" discusses a wearable dual-wavelength diffuse speckle contrast flow oximetry (DSCFO) device for simultaneous measurements of blood flow and oxygenation variation in deep tissues. Moreno et al. (2019), "Evaluation on Phantoms of the Feasibility of a Smart Bra to Detect Breast Cancer in Young Adults", discloses the use of breast tissue phantoms to investigate the feasibility of quantifying breast density and detecting breast cancer tumors using a smart bra. Pinti et al., (2018), "A Review on the Use of Wearable Functional Near-Infrared Spectroscopy in Naturalistic Environments" reviews the use of wearable fNIRS in naturalistic settings in the field of cognitive neuroscience. Rahman et al., (2016), "Electromagnetic Performances Analysis of an Ultra-Wideband and Flexible Material Antenna in Microwave Breast Imaging: To Implement a Wearable Medical Bra" discloses a compact and ultra-wide band antenna on a flexible substrate for microwave imaging. Ray et al. (2017), "A Systematic Review of Wearable Systems for Cancer Detection: Current State and Challenges" reviews cancer detection using wearable systems, including sensor-based smart systems with a microcontroller, Bluetooth module, and smart phone.

Robbins et al., (2021), "Two-Layer Spatial Frequency Domain Imaging of Compression-Induced Hemodynamic Changes in Breast Tissue" studied hemodynamic changes in response to localized breast compression using a handheld SFDI device. Roblyer et al., (2020b), "Tracking Breast Cancer Therapies with Handheld and Wearable Diffuse Optics" disclose an NIR-II imaging system, "Detection of Optically Luminescent Probes using Hyperspectral and Diffuse Imaging in Near-infrared" (DOLPHIN) for noninvasive real-time tracking of a 0.1 mm-sized fluorophore through the gastrointestinal tract of a mouse. Shokoufi et al. (2017), "Novel Handheld Diffuse Optical Spectroscopy Probe for Breast Cancer Assessment: Clinical Study", discloses a hand-held continuous-wave radio-frequency modulated diffuse optical spectroscopy probe.

Spink et al., (2020), "High Optode-Density Wearable Probe for Monitoring Breast Tumor Dynamics During Neoadjuvant Chemotherapy" disclose an NIR-II imaging system, "Detection of Optically Luminescent Probes using Hyperspectral and diffuse Imaging in Near-infrared" (DOLPHIN). Spink et al., (2021), "High Optode-Density Wearable Diffuse Optical Probe for Monitoring Paced Breathing Hemodynamics in Breast Tissue" discloses a high optode-density wearable continuous wave diffuse optical probe for the monitoring of breathing hemodynamics in breast tissue.

Teng et al., (2017), "Wearable Near-Infrared Optical Probe for Continuous Monitoring During Breast Cancer Neoadjuvant Chemotherapy Infusions" presents a new continuous-wave wearable diffuse optical probe for investigating the hemodynamic response of locally advanced breast cancer patients during neoadjuvant chemotherapy infusions. Teng, (2018), "A Wearable Near-Infrared Diffuse Optical System for Monitoring in Vivo Breast Tumor Hemodynamics During Chemotherapy Infusions" discloses a new wearable diffuse optical device to investigate if very early time-points during a patient's first chemotherapy infusion are predictive of overall response (pCR versus non-pCR) to NAC. Wang et al., (2020), "Development of a Prototype of a Wearable Flexible Electro-Optical Imaging System for the Breast" discloses a wearable breast imaging system which combines a garment and a flexible electronic system.

Ahmed et al., (2021), "Differential Optical Absorption Spectroscopy-Based Refractive Index Sensor for Cancer Cell Detection" discloses a spectroscopic optical sensor for cancerous cell detection in various parts of the human body. Altoe et al., (2019), "Diffuse Optical Tomography of the Breast: A Potential Modifiable Biomarker of Breast Cancer Risk with Neoadjuvant Chemotherapy" studied whether a diffuse optical tomography breast imaging system (DOT-BIS) can provide a comparable optical-based image index of mammographic breast density. Altoe et al., (2021), "Changes in Diffuse Optical Tomography Images During Early Stages of Neoadjuvant Chemotherapy Correlate with Tumor Response in Different Breast Cancer Subtypes" studied changes in optically derived parameters acquired with a diffuse optical tomography breast imaging system (DOTBIS) in the tumor volume of patients with breast carcinoma receiving neoadjuvant chemotherapy (NAC). Altoe et al., (2021), "Effects of Neoadjuvant Chemotherapy on the Contralateral Non-Tumor-Bearing Breast Assessed by Diffuse Optical Tomography" studied whether changes in optically derived parameters acquired with a diffuse optical tomography breast imager system (DOTBIS) in the contralateral non-tumor-bearing breast in patients administered neoadjuvant chemotherapy (NAC) for breast cancer are associated with pathologic complete response (pCR).

Anderson et al., (2017), "Optical Mammography in Patients with Breast Cancer Undergoing Neoadjuvant Chemotherapy: Individual Clinical Response Index" discloses an optical mammography study to develop quantitative measures of pathologic response to neoadjuvant chemotherapy (NAC) in patients with breast cancer. Angelo et al., (2018), "Review of Structured Light in Diffuse Optical Imaging" discloses diffuse optical imaging probes in living tissue enabling structural, functional, metabolic, and molecular imaging. Applegate et al., (2018), "Multi-Distance Diffuse Optical Spectroscopy with a Single Optode via Hypotrochoidal Scanning" studied a new method of frequency-domain diffuse optical spectroscopy (FD-DOS) to rapidly acquire a wide range of source-detector (SD) separations by mechanically scanning a single SD pair.

Chae et al., (2020), "Development of Digital Breast Tomosynthesis and Diffuse Optical Tomography Fusion Imaging for Breast Cancer Detection" studied a new digital breast tomosynthesis (DBT)/DOT fusion imaging technique for breast cancer detection. Cochran et al., (2019), "Hybrid Time-Domain and Continuous-Wave Diffuse Optical Tomography Instrument with Concurrent, Clinical Magnetic Resonance Imaging for Breast Cancer Imaging" discusses diffuse optical tomography (DOT) for three-dimensional (3-D) maps of tissue optical and physiological properties in human tissue. Durduran et al. (2010), "Diffuse Optics for Tissue Monitoring and Tomography" discloses using near-infrared or diffuse optical spectroscopy to measure tissue hemodynamics.

Fakayode et al., (2020), "Molecular (Raman, NIR, and FTIR) Spectroscopy and Multivariate Analysis in Consumable Products Analysis" reviews the use of Raman, near-infrared (NIR), and Fourier-transform infrared (FTIR) spectrometers to evaluate consumable products such as food. Fantini et al., (2001), "Optical Spectroscopy and Imaging of Tissues" studies development of new improved methods and instrumentation for biomedical applications of near-infrared spectroscopy and imaging. Fantini (2005), "Optical Spectroscopy and Imaging of Tissues", NSF Award, 2005 (abstract only viewed), researched techniques for optical spectroscopy and imaging of biological tissues. Fantini et al., (2012), "Near-Infrared Optical Mammography for Breast Cancer Detection with Intrinsic Contrast" reviews optical methods to detect breast cancer on the basis of increased opacity. Farmani et al., (2020), "Optical Nanosensors for Cancer and Virus Detections" discusses photonic crystal (PhC)-based optical nanosensors.

Flexman et al., (2008), "The Design and Characterization of a Digital Optical Breast Cancer Imaging System" discusses how optical imaging has the potential to play a major role in breast cancer screening and diagnosis due to its ability to image cancer characteristics such as angiogenesis and hypoxia. Ghijsen et al., (2018), "Quantitative Real-Time Optical Imaging of the Tissue Metabolic Rate of Oxygen Consumption" discloses a noncontact method for quantitatively mapping tMRO2 over a wide, scalable field of view. Grosenick et al. (2016), "Review of Optical Breast Imaging and Spectroscopy reviews the monitoring neoadjuvant chemotherapy and breast cancer risk assessment via optical breast imaging and spectroscopy. Gunther et al. (2018), "Dynamic Diffuse Optical Tomography for Monitoring Neoadjuvant Chemotherapy in Patients with Breast Cancer" identifies dynamic optical imaging features associated with pathologic response in patients with breast cancer during neoadjuvant chemotherapy.

Hoi et al., (2018), "Non-Contact Dynamic Diffuse Optical Tomography Imaging System for Evaluating Lower Extremity Vasculature" discloses a multi-view non-contact dynamic diffuse optical tomographic imaging system for the clinical evaluation of vasculature in the lower extremities. Imamura et al., (2018), "In Vivo Optical Imaging of Cancer Cell Function and Tumor Microenvironment" discusses in vivo optical imaging using fluorescence and bioluminescence. Intes et al., (2004), "Time-Domain Optical Mammography Softscan: Initial Results on Detection and Characterization of Breast Tumors" presents initial results obtained using a breast-imaging system developed by Advanced Research Technologies comprising a 4-wavelength time-resolved scanning system. Jeong et al., (2020), "Emerging Advanced Metasurfaces: Alternatives to Conventional Bulk Optical Devices" discusses the use of optical metasurfaces as color filters, metalenses, beam generators or splitters, and metaholograms.

Joshi et al., (2018), "Targeted Optical Imaging Agents in Cancer: Focus on Clinical Applications" discusses molecular imaging for in vivo visualization of cancer over time based on biological mechanisms of disease activity Khan (2013), "Image Reconstruction in Diffuse Optical Tomography With Sparsity Constraints", NSF Award, 2013 (abstract only viewed), researched the use of sparsity-constrained regularization for solving the diffuse optical tomography inverse problem. Kim et al. (2016), "US-Localized Diffuse Optical Tomography in Breast Cancer: Comparison With Pharmacokinetic Parameters of DCE-MRI and With Pathologic Biomarkers" discloses correlating parameters of ultrasonography-guided diffuse optical tomography with the pharmacokinetic features of dynamic contrast-enhanced MRI and pathologic markers of breast cancer. Koetse et al., (2007), "Optical Sensor Array Platform Based on Polymer Electronic Devices" discusses devices based on polymer semiconductors fabricated with thin film technology.

Krishnamurthy, (2018), "Using Near-Infrared Spectroscopy to Study Static and Dynamic Hemoglobin Contrast Associated with Breast Cancer" discloses an instrument for diffuse optical mammography with parallel plate geometry. Leo et al., (2017), "Optical Imaging of the Breast: Basic Principles and Clinical Applications" summarizes the physical principles, technology features, and first clinical applications of optical imaging techniques to the breast. Li et al., (2018), "Sensitive and Wearable Optical Microfiber Sensor for Human Health Monitoring" discloses a sensor with a hybrid plasmonic microfiber knot resonator embedded in a polydimethylsiloxane membrane.

Liu et al., (2018), "Diffuse Optical Spectroscopy for Monitoring the Responses of Patients with Breast Cancer to Neoadjuvant Chemotherapy: A Meta-Analysis" investigated the potential of diffuse optical spectroscopy (DOT) for monitoring the responses of patients with breast cancer to neoadjuvant chemotherapy (NAC). Liu et al., (2020), "Recent Progress in Flexible Wearable Sensors for Vital Sign Monitoring" discusses the development of flexible electronic materials, as well as the wide development and application of smartphones, the cloud, and wireless systems, flexible wearable sensor technology. Lutzweiler et al. (2013), "Optoacoustic Imaging and Tomography: Reconstruction Approaches and Outstanding Challenges in Image Performance and Quantification" reviews optoacoustic imaging from image reconstruction and quantification perspectives. Ma et al., (2020b), "Fiber-Free Parallel-Plane Continuous Wave Breast Diffuse Optical Tomography System" discusses near infrared diffuse optical tomography (DOT) for detecting breast cancer.

Mabou et al. (2018), "Breast Cancer Detection Using Infrared Thermal Imaging and a Deep Learning Model" discloses the use of infrared digital imaging for breast cancer detection based on thermal comparison between a healthy breast and a breast with cancer. Nguyen et al., (2020), "Preliminary Development of Optical Computed Tomography (Optical CT) Scanner Using Transillumination Imaging NAD" discusses the use of near-infrared transillumination imaging for biomedical applications such as human biometrics and animal experiments. Pan et al., (2020), "A Multifunctional Skin-Like Wearable Optical Sensor Based on an Optical Micro-/Nanofibre" discusses multifunctional skin-like sensors for next-generation healthcare, robotics, and bioelectronics.

Park et al., (2013), "Multispectral Imaging with Vertical Silicon Nanowires" reports on the demonstration of a compact multispectral imaging system that uses vertical silicon nanowires for a filter array. Park et al., (2015), "Vertically Stacked Photodetector Devices Containing Silicon Nanowires with Engineered Absorption Spectra" discloses a vertically stacked photodetector device containing silicon nanowire photodetectors formed above a silicon substrate that also contains a photodetector. Perumal et al., (2019), "Near Infra-Red Polymeric Nanoparticle Based Optical Imaging in Cancer Diagnosis" reviews the recent progress in NIRF polymeric nanoparticles used for optical imaging particularly on cancer diagnosis. Qiu (2018), "Implantable Ultra-low Power VO2 MEMS Scanner Based Surface-Enhanced Raman Spectroscope for Wide-field Tumor Imaging in Free Moving Small Animals", NSF Award, 2018 (abstract only viewed) discloses tumor-targeting surface enhanced Raman scattering nanoparticles based on multiplexed Raman spectroscopy.

Soliman et al. (2010), "Functional Imaging Using Diffuse Optical Spectroscopy of Neoadjuvant Chemotherapy Response in Women with Locally Advanced Breast Cancer" discloses functional imaging with tomographic near-infrared diffuse optical spectroscopy to measure tissue concentration of deoxyhemoglobin, oxyhemoglobin, percent water, and scattering power. Tank et al., (2020), "Diffuse Optical Spectroscopic Imaging Reveals Distinct Early Breast Tumor Hemodynamic Responses to Metronomic and Maximum Tolerated Dose Regimens" reports on a dual-center study which examined 54 breast tumors receiving NAC measured with DOSI before therapy and the first week following chemotherapy administration.

Tromberg et al. (2016), "Predicting Responses to Neoadjuvant Chemotherapy in Breast Cancer: ACRIN 6691 Trial of Diffuse Optical Spectroscopic Imaging" investigates whether changes from baseline to mid-therapy in a diffuse optical spectroscopic imaging (DOSI)-derived imaging endpoint, the tissue optical index, predict pathologic complete response in women undergoing breast cancer neoadjuvant chemotherapy. Uddin et al., (2020a), "Optimal Breast Cancer Diagnostic Strategy Using Combined Ultrasound and Diffuse Optical Tomography" presents a two-stage diagnostic strategy that is both computationally efficient and accurate. Upputuri, (2019), "Photoacoustic Imaging in the Second Near-Infrared Window: A Review" discusses photoacoustic (PA) imaging that combines optical excitation and ultrasound detection.

Vavadi et al., (2018), "Compact Ultrasound-Guided Diffuse Optical Tomography System for Breast Cancer Imaging" discusses an ultrasound-guided DOT system. Yu et al., (2010), "Near-Infrared, Broad-Band Spectral Imaging of the Human Breast for Quantitative Oximetry: Applications to Healthy and Cancerous Breasts" discusses the examination of ten human subjects with a previously developed instrument for near-infrared diffuse spectral imaging of the female breast. Yuan et al., (2014), "Light-Emitting Diode-Based Multiwavelength Diffuse Optical Tomography System Guided by Ultrasound" discloses a low-cost DOT system using LEDs of four wavelengths in the NIR spectrum as light sources.

Zhang et al., (2020), "Efficacy of Shear-Wave Elastography Versus Dynamic Optical Breast Imaging for Predicting the Pathological Response to Neoadjuvant Chemotherapy in Breast Cancer" discusses the value of shear-wave elastography (SWE) parameters and dynamic optical breast imaging features for predicting pathological responses to neoadjuvant chemotherapy (NACT) in breast cancer (BC). Zhu et al., (2020), "A Review of Optical Breast Imaging: Multi-Modality Systems for Breast Cancer Diagnosis" reviews optical breast imaging using multi-modality platforms. Zhu et al., (2021), "Early Assessment Window for Predicting Breast Cancer Neoadjuvant Therapy Using Biomarkers, Ultrasound, and Diffuse Optical Tomography" assesses the utility of tumor biomarkers, ultrasound (US) and US-guided diffuse optical tomography (DOT) in early prediction of breast cancer response to neoadjuvant therapy (NAT).

SUMMARY OF THE INVENTION

This invention is a smart bra for optical scanning of breast tissue which can help in early detection of abnormal tissue. It can have advantages over current screening methods such as conventional mammography because it involves less exposure to potentially-harmful ionizing radiation and less discomfort. It can also enable easier periodic longitudinal tracking of tissue changes over time. This smart bra has light emitters which transmit light into breast tissue and light receivers which receive the light after it has been transmitted through the breast tissue. Spectroscopic analysis of the light received can help to detect the presence, composition, shape, size, and/or location of abnormal tissue.

One of the challenges in optical scanning of breast tissue is air gaps between light emitters and/or receivers and the surface of a breast which can reduce scanning accuracy. The smart bra disclosed herein addresses this challenge by selectively adjusting the fit of the bra to the contour of a breast, thereby closing air gaps. The fit of the smart bra is adjusted by the selective expansion of individual expandable components connected to light emitters and/or receivers. The expandable components selectively move light emitters and/or receivers closer to the surface of a breast where needed to close air gaps on a cup, without causing tightness or discomfort in other areas of the cup. In an example, expandable components can be bladders which are filled with a flowable substance such as air or water. Alternatively, expandable components can be electromagnetic actuators.

INTRODUCTION TO THE FIGURES

Figure 2:
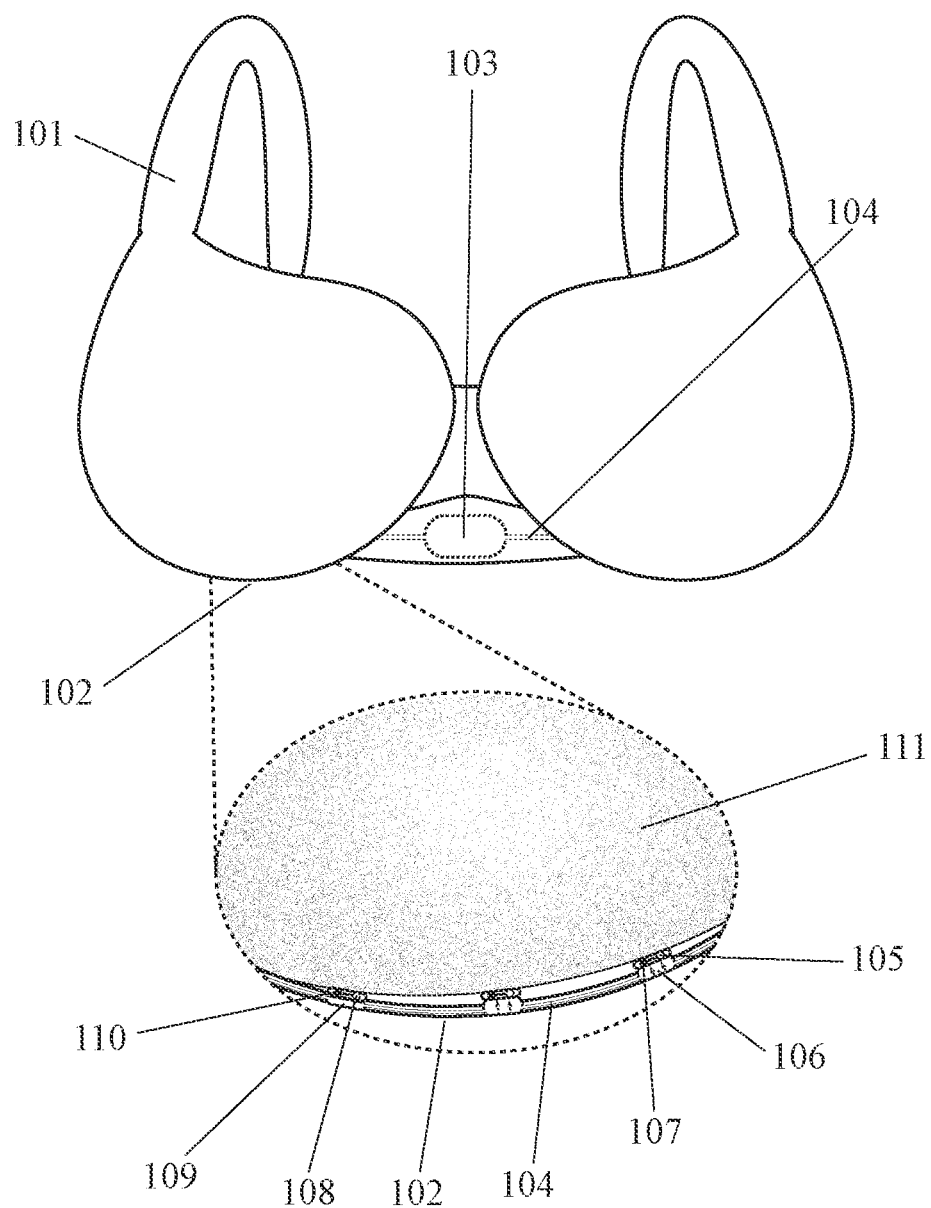

FIGS. 1 and 2 show a smart bra with optical components (e.g. light emitters and receivers) and expandable components which move those optical components, wherein the expandable components are bladders filled with a gas or liquid. FIG. 1 shows this smart bra before the fit of the bra has been adjusted to close air gaps between optical components and the surface of the breast. FIG. 2 shows this smart bra after the fit of the bra has been adjusted to close air gaps.

Figure 3:
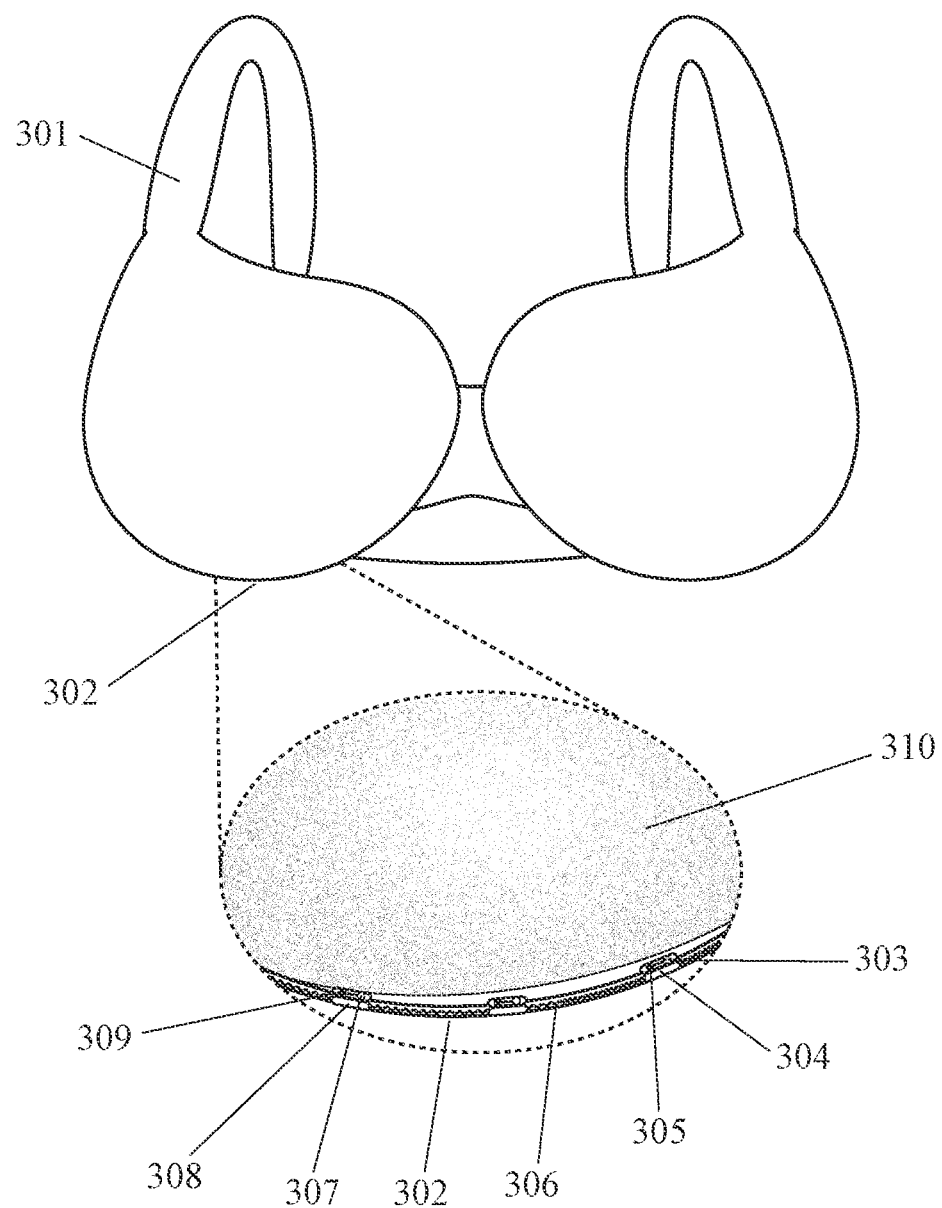
Figure 4:
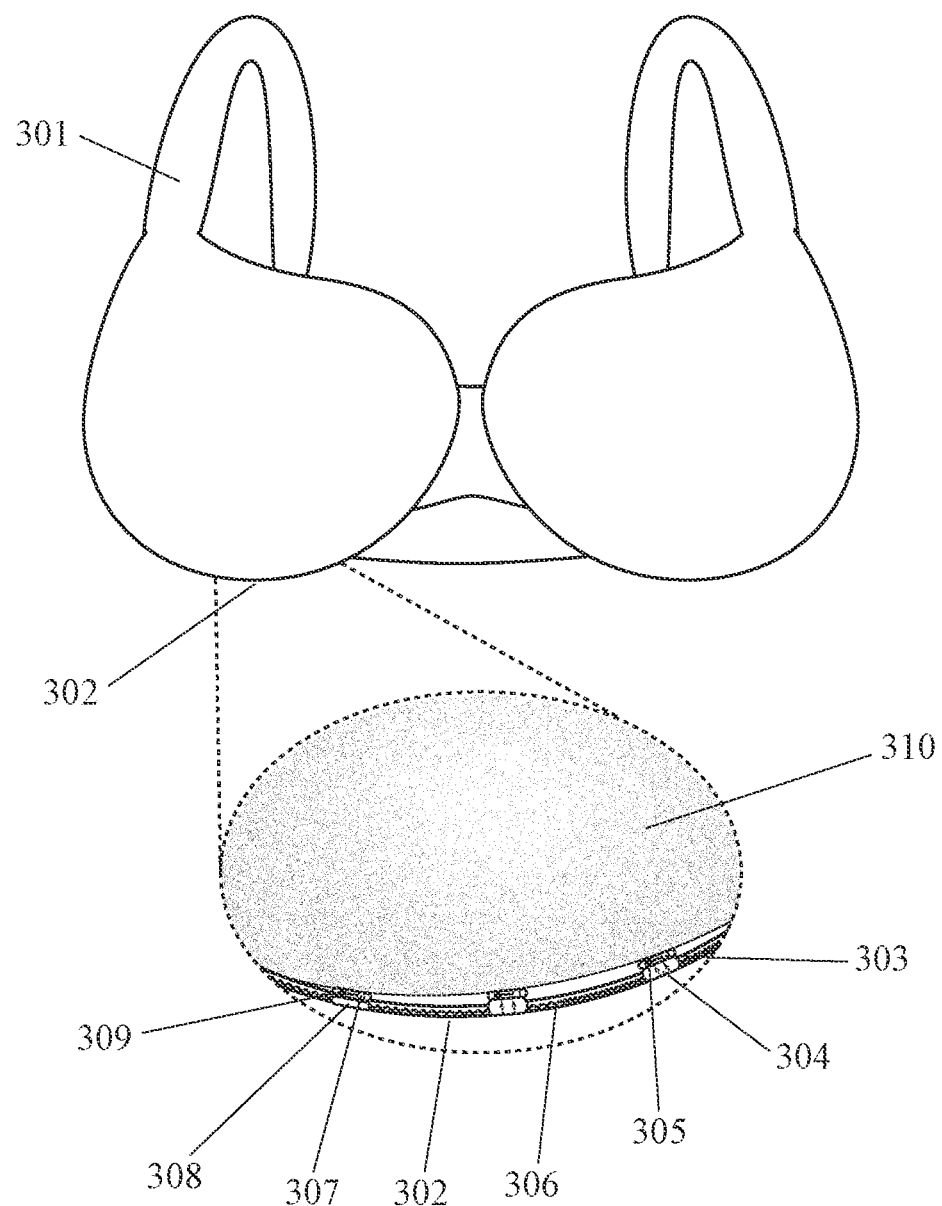

FIGS. 3 and 4 show a smart bra with optical components (e.g. light emitters and receivers) and expandable components which move those optical components, wherein the expandable components are electromagnetic actuators. FIG. 3 shows this smart bra before the fit of the bra has been adjusted to close air gaps between optical components and the surface of the breast. FIG. 4 shows this smart bra after the fit of the bra has been adjusted to close air gaps.

Figure 5:
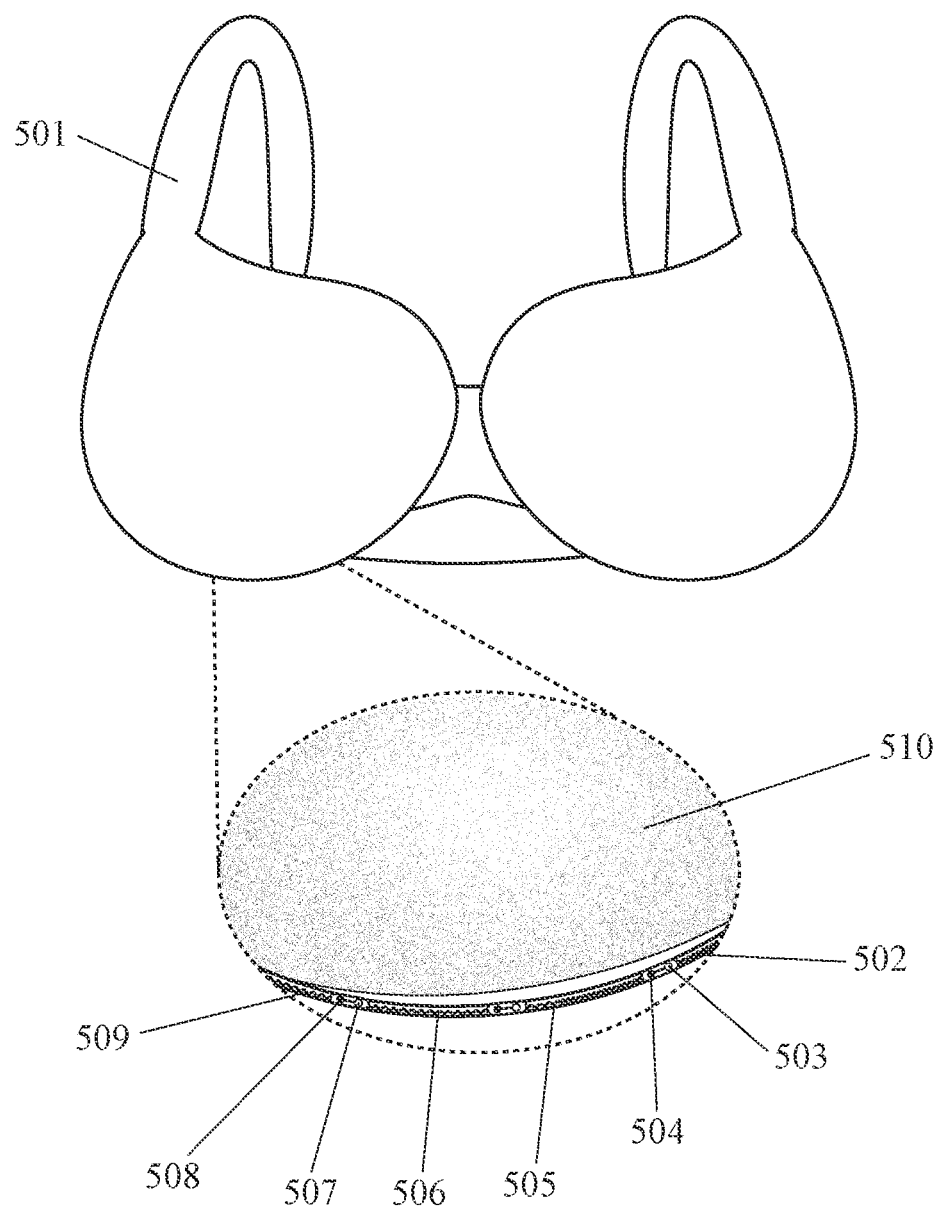
Figure 6:
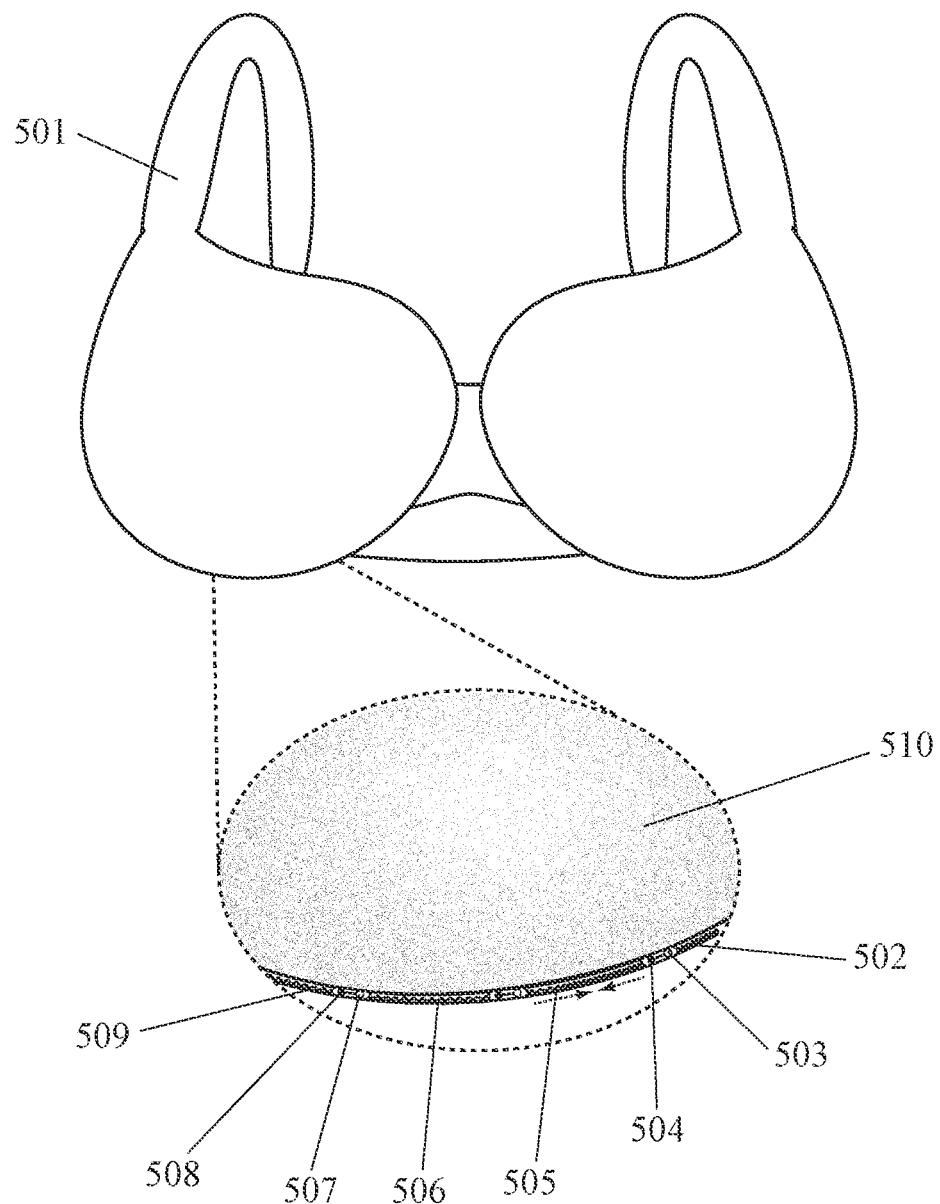

FIGS. 5 and 6 show a smart bra with optical components (e.g. light emitters and receivers) and piezoelectric components which move those optical components. FIG. 5 shows this smart bra before the fit of the bra has been adjusted to close air gaps between optical components and the surface of the breast. FIG. 6 shows this smart bra after the fit of the bra has been adjusted to close air gaps.

Figure 7:
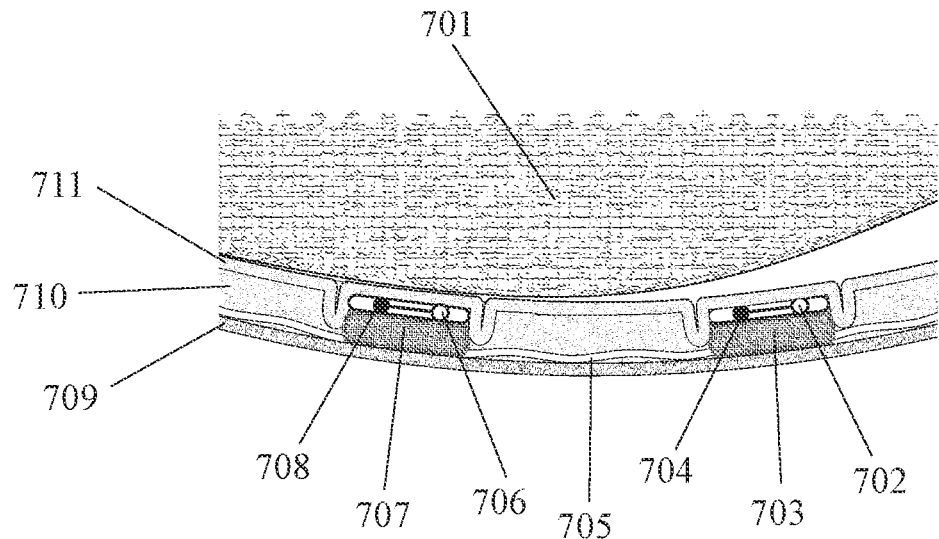
Figure 8:
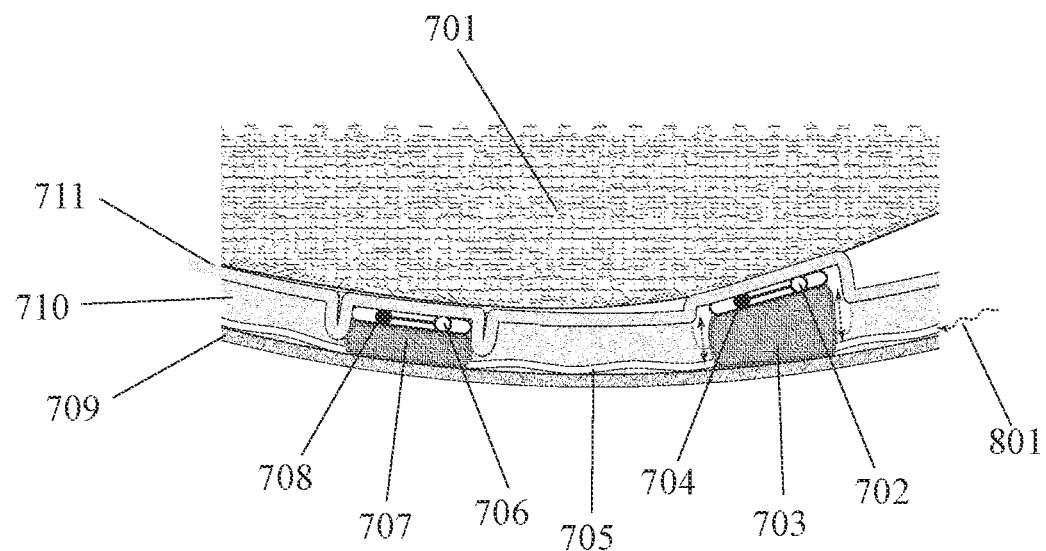

FIGS. 7 and 8 show a close-up cross-sectional view of a section of a smart bra with optical components and expandable components. FIG. 7 shows this smart bra before the fit of the bra has been adjusted to close air gaps between optical components and the surface of the breast. FIG. 8 shows this smart bra after the fit of the bra has been adjusted to close air gaps.

DETAILED DESCRIPTION OF THE FIGURES

FIGS. 1 and 2 show views, at two different times, of a smart bra for spectroscopic scanning of breast tissue to help detect abnormal tissue. FIG. 1 shows this smart bra at a first time, before the fit of the bra has been adjusted to close any air gaps between optical scanning components and the surface of a breast. FIG. 2 shows this smart bra at a second time, after the fit of the bra has been adjusted to close any air gaps between optical scanning components and the surface of the breast. The upper portions of FIGS. 1 and 2 shows opaque frontal views of the smart bra. The lower portions of FIGS. 1 and 2 show a dotted-line ellipse, within which are cross-sectional close-up views of a lower portion of a cup. This close-up view shows optical components, expandable components, a lower a portion of the breast, and some air gaps between the optical components and the surface of the breast. The air gaps are open in FIG. 1, but are closed by the device in FIG. 2.

The smart bra shown in FIGS. 1 and 2 can be described as a smart bra for spectroscopic scanning of breast tissue to help detect abnormal tissue comprising: (i) a bra with two cups which is configured to be worn on a person's breasts, wherein an interior surface of a cup faces toward the person's breast and an exterior surface of the cup faces away from the person's breast; (ii) a first optical component on the interior surface of the cup, wherein the first optical component comprises a light emitter which transmits light into the person's breast and/or a light receiver which receives light which has been transmitted (e.g. reflected or side-to-side transmitted) through the person's breast, wherein the first optical component is a first distance from the surface of the person's breast in a first configuration and a second distance from the surface of the person's breast in a second configuration, and wherein a first distance adjustment is the first distance minus the second distance; (iii) a first expandable component, wherein expansion of the first expandable component moves the first optical component from the first configuration to the second configuration; (iv) a second optical component on the interior surface of the cup, wherein the second optical component comprises a light emitter which transmits light into the person's breast and/or a light receiver which receives light which has been transmitted (e.g. reflected or side-to-side transmitted) through the person's breast, wherein the second optical component is a third distance from the surface of the person's breast in the first configuration and a fourth distance from the surface of the person's breast in the second configuration, wherein a second distance adjustment is the third distance minus the fourth distance, and wherein the second distance adjustment is greater than the first distance adjustment; and (v) a second expandable component, wherein expansion of the second expandable component moves the second optical component from the first configuration to the second configuration.

With respect to specific components, the smart bra shown in FIGS. 1 and 2 comprises: (i) a bra 101 with two cups which is configured to be worn on a person's breasts, wherein an interior surface of a cup faces toward the person's breast 111 and an exterior surface 102 of the cup faces away from the person's breast; (ii) a first optical component on the interior surface of a cup, wherein the first optical component comprises a light emitter 108 which transmits light into the person's breast and a light receiver 110 which receives light which has been transmitted (e.g. reflected or side-to-side transmitted) through the person's breast, wherein the first optical component is a first distance from the surface of the person's breast in a first configuration (shown in FIG. 1) and a second distance from the surface of the person's breast in a second configuration (shown in FIG. 2), and wherein a first distance adjustment is the first distance minus the second distance; (iii) a first expandable component 109, wherein expansion of the first expandable component moves the first optical component from the first configuration to the second configuration; (iv) a second optical component on the interior surface of the cup, wherein the second optical component comprises a light emitter 105 which transmits light into the person's breast and a light receiver 107 which receives light which has been transmitted (e.g. reflected or side-to-side transmitted) through the person's breast, wherein the second optical component is a third distance from the surface of the person's breast in the first configuration (shown in FIG. 1) and a fourth distance from the surface of the person's breast in the second configuration (shown in FIG. 2), wherein a second distance adjustment is the third distance minus the fourth distance, and wherein the second distance adjustment is greater than the first distance adjustment; and (v) a second expandable component 106, wherein expansion of the second expandable component moves the second optical component from the first configuration to the second configuration.

The smart bra which is shown in FIGS. 1 and 2 further comprises a pump 103 on the back strap of the bra which pumps a flowable substance through a tube or channel 104 into the first expandable component and the second expandable component. In the example shown in FIGS. 1 and 2, expandable components are air bladders which are expanded by inflation with a gas (e.g. air). In another example, expandable components can be liquid bladders which are expanded by being filled with a liquid (e.g. water).

In FIG. 1, a first optical component (comprising light emitter 108 and light receiver 110) has close contact with the surface of breast tissue 111 and no associated air gap. However, there is an air gap between the second optical component (comprising light emitter 105 and light receiver 107) and the surface of the breast tissue. An air gap such as this can cause errors in optical (e.g. spectroscopic) scanning of breast tissue. In FIG. 2, a second expandable component 106 has been selectively expanded, thereby pushing the second optical component toward the surface of the breast tissue. This movement closes the air gap, reducing potential errors in optical scanning of the breast tissue. Differential expansion of the second expandable component relative to the first expandable component helps this smart bra to conform to the shape of the breast where there are air gaps, without causing undue tightness or discomfort where there are no air gaps.

In an example, a smart bra can be made and sold in standard bra sizes (e.g. standard chest and cup sizes). In an example, a smart bra can be made with a stretchable, elastic, flexible, and/or conforming material (e.g. stretchable, elastic, flexible, and/or conforming fabric). In an example, a smart bra can have optical components and expandable components on both cups in order to optically scan both breasts. In an example, results from optical scanning of right and left breasts can be compared with each other and/or contrasted to help detect abnormal breast tissue. One breast can act as a reference for the detecting abnormalities in the other breast. Also, results from a current scan can be compared and/or contrasted with results from a past scans to help detect abnormal breast tissue. A past scan can act as a reference for detecting abnormalities in a current scan.

In an example, an optical component can further comprise one or more sub-components selected from the group consisting of: a light emitter, a light receiver, a mirror, a micromirror array, a lens, an optical filter, a prism, a gimbal mechanism, and an electromagnetic actuator. In an example, a smart bra can further comprise additional electronic and mechanical components which are located on the back strap of the bra. In an example, additional electronic and mechanical components can be selected from the group consisting of: a battery; a data processor; a memory; a wireless data transmitter; a wireless data receiver; a manual air or liquid pump; an automated air or liquid pump; and an air or liquid reservoir.

In an example, a smart bra can be worn for a short period of time on a periodic (e.g. annual, monthly, weekly, or daily) basis in order to obtain a periodic longitudinal time series of optical scans of breast tissue. This can be useful for identifying potential changes in tissue composition over time which could indicate abnormal tissue growth. Alternatively, a smart bra can be worn as a regular undergarment during everyday life for continuous monitoring and optical scanning during different activities during the day. In an example, data from light receivers in a smart bra can be transmitted to a separate data processor for spectroscopic analysis to identify changes in breast tissue composition and/or help identify abnormal breast tissue. In an example, data from a smart bra can be (wirelessly) transmitted to a data processor in a different wearable device (e.g. a smart watch), a handheld device (e.g. a cell phone), or a remote server (e.g. in a healthcare provider's server and/or cloud storage).

In an example, a cup on a smart bra can have three layers. The first layer is an interior layer which faces toward the surface of a person's breast. In an example, this interior layer can be elastic, stretchable, and/or flexible. In an example, this interior layer can also be transparent. In an example, this interior layer can be less than 3 mm thick. If this interior layer is not transparent, then there can be holes in the interior layer through which optical components can (movably) protrude for closer optical communication with the surface of a breast.

The second layer is a middle layer. In an example, the middle layer can be between 1 mm and 5 mm thick. In an example, this middle layer can contain expandable components. In an example, expandable components can be air bladders or chambers. In an example, expandable components can be fluid bladders or chambers. In an example, expandable components can be electromagnetic actuators. In an example, the middle layer can be soft and compressible, with holes in which the expandable components are located.

The third layer is the exterior layer. In an example, the exterior layer can be between 1 mm and 4 mm thick. In an example, this exterior layer can be less elastic, stretchable, or flexible than the first layer. In an example, this exterior layer can be opaque in order to reduce penetration of light from the environment into the cup and/or to reduce the escape of light from the light emitters out of the cup.

In an example, an optical component can comprise a light emitter which transmits light into breast tissue. In an example, an optical component can comprise a light receiver (e.g. photodetector) which receives light after it has been transmitted through breast tissue. In an example, an optical component can comprise both a light emitter and a light receiver. In an example, an optical component can comprise one light emitter and a plurality of light receivers. In an example, an optical component can comprise one light emitter and a plurality of light receivers around the light emitter. In an example, an optical component can comprise one light receiver and a plurality of light emitters. In an example, an optical component can comprise one light receiver and a plurality of light emitters around the light receiver.

The term "transmitted" as used herein with respect to light includes light which has been reflected back from a relatively-shallow layer of breast tissue as well as light which has been transmitted from one surface (e.g. the right side) of a breast to another surface (e.g. the left side) of the breast. In both cases, light has been "transmitted" through breast tissue to some extent. This inclusive definition of "transmitted" light is used herein because there are definitional problems in trying to otherwise distinguish between "reflected" and "transmitted" light when it comes to optical scanning of the breast. If one were to try to distinguish between "reflected" and "transmitted light based on tissue depth, then how far below the outermost skin layer would light have to penetrate before light is called "transmitted" rather than "reflected"—1 nm? 1 mm? 5 mm? 10 mm? 50 mm? Alternatively, if one were to try to distinguish between "reflected" and "transmitted" light based on distance between a light emitter and a light receiver, then how far apart would they have to be before light is called "transmitted" rather than "reflected"? Due to these definitional ambiguities, the term "transmitted" as used generally herein to describe light which has been transmitted through breast tissue at least to some extent; this includes light which is sometimes called "reflected" in the prior art as well as light which is sometimes called "transmitted" in the prior art.

In an example, a light emitter can be an LED (Light Emitting Diode). In an example, a light emitter can emit coherent light. In an example, a light emitter can emit polarized light. In an example, a light emitter can emit light at a constant frequency and/or in a constant spectral range. In an example, a light emitter can emit light at a frequency and/or a spectral range which varies over time. In an example, a light emitter can emit light in pulses. In an example, a light emitter can emit light at a constant angle and/or focal vector. In an example, a light emitter can emit light at an angle and/or along a focal vector which varies over time. In an example, an optical component can include an electromagnetic actuator which changes the angle and/or focal vector of light emission over time.

In an example, an LED can be selected from the group consisting of: encapsulated LED, infrared LED, monochromatic LED, near-infrared LED, organic light emitting diode (OLED), resonant cavity light emitting diode (RCLED), super-luminescent light emitting diode (SLED), and tunable LED. In an example, light emitters can be lasers. In an example, a laser can be selected from the group consisting of: continuous-wave laser, green-light laser, infrared laser, laser, laser diode, multi-wavelength laser, pulsatile laser, red-light laser, super-luminescent laser, and ultraviolet laser. In an example, a light emitter can be a coherent light emitter, an infrared light emitter, a near-infrared light emitter, and an ultraviolet light emitter. In an example, a light emitter can emit light with a frequency between 763 and 768 nm. In an example, a light emitter can emit light with a frequency between 1398 and 1403 nm.

In an example, a light receiver can be selected from the group consisting of: photodetector, photoresistor, avalanche photodiode (APD), charge-coupled device (CCD), complementary metal-oxide semiconductor (CMOS), infrared detector, infrared photoconductor, infrared photodiode, light dependent resistor (LDR), optoelectric sensor, photoconductor, photodiode, photomultiplier, and phototransistor. In an example, a smart bra can comprise a plurality of stacked photodetectors, multi-layer photodetectors, and/or vertical nanowire arrays which receive light after it has passed through breast tissue. In an example, a light receiver can be a avalanche photo diode (APDs) or PIN photodiode.

In an example, angles between the focal vectors of light beams emitted from light emitters and the surface of a breast can vary with the distance of those light emitters from the apex of a cup. In an example, these angles can be correlated with, or even proportional to, this distance. In an example, angles between the focal vectors of light emitted from light emitters and the surface of a breast can decrease with the distance of the light emitters from the apex of a cup. In an example, angles between the focal vectors of light emitted from light emitters which are closer to the apex of a cup can be more perpendicular relative to the surface of a breast than the focal vectors of light emitted from light emitters which are farther from the apex of the cup.

In an example, an array of optical components can be configured in several (e.g. 3 to 10) nested and/or concentric (circular, elliptical, or cardioid shaped) rings on the cup of a smart bra. In an example, an array of optical components can be configured in several (e.g. 6 to 24) to radial spokes on the cup of a smart bra. In an example, an array of optical components can be configured in a spiral and/or helix pattern on the cup of a smart bra. In an example, there can be a pattern of alternating light emitters and light receivers along a ring, radial spoke, spiral, or helix. In an example, light emitters can be clustered on one side (or quadrant) or a breast and light emitters can be clustered on the opposite side (or quadrant) of the breast, or vice versa. In an example, there can be between 5 and 20 optical components in a cup of a smart bra. In an example, there can be between 10 and 100 optical components in a cup of a smart bra. In an example, there can be more than 50 optical components in a cup of a smart bra.

In an example, optical components can be on the interior surface of a cup. In an example, optical components can be in direct optical communication with the surface of a person's breast. Alternatively, optical components can be separated from the surface of a breast by a transparent layer which transmits light, but protects the optical components when a smart bra is washed. In an example, a transparent layer can be made with a transparent elastomeric material. In an example, a transparent layer can be made with a transparent silicone-based material, such as PDMS.

In an example, optical components can be removably-attached to a smart bra (e.g. by a clip, clasp, or hook-and-eye material) so that they can be removed before the bra is washed. In an example, there can be an opaque layer between optical components and the exterior surface of a cup to isolate light receivers from ambient light and to prevent light from light emitters from shining out of the cup. In an example, an optical component can be attached to a cup by a gimbal mechanism which enables the component to tilt in order to better conform to a breast surface.

In an example, light from a light emitter which has been transmitted through breast tissue (by reflection or side-to-side transmission) and received by a light receiver can be spectroscopically analyzed to detect the presence, composition, shape, size, and/or location of abnormal breast tissue. In an example, changes in the spectral distribution and/or spectrum of transmitted light can be analyzed to detect the presence, composition, shape, size, and/or location of abnormal breast tissue. In an example, spectral changes of light transmitted between a plurality of pairs of light emitters and light receivers can be collectively analyzed (e.g. triangulated) in order to identify the likely location of abnormal breast tissue.

In an example, light which has been transmitted through breast tissue from different light emitters at different times can be jointly analyzed in order to identify the presence, composition, shape, size, and/or location of abnormal tissue. In an example, light which has been transmitted through breast tissue between different pairs of light emitters and light receivers (at different times) can be jointly analyzed in order to identify the presence, composition, shape, size, and/or location of abnormal tissue. In an example, light which has been transmitted through breast tissue between different pairs of light emitters and light receivers (at different times) can be triangulated in order to identify the presence, composition, shape, size, and/or location of abnormal tissue.

In an example, light which has been transmitted through breast tissue between different pairs of light emitters and light receivers (at different times) can be jointly analyzed using multivariate analysis in order to identify the presence, composition, shape, size, and/or location of abnormal tissue. In an example, the intersection of light beams traveling along different vectors through breast tissue can be used to triangulate the location (and size and shape) of abnormal breast tissue.

In an example, light which has been transmitted through breast tissue and received by light receivers can be analyzed to identify the presence, composition, shape, size, and/or location of abnormal tissue in the breast based on analysis of one or more of the following biometric markers: hemoglobin, deoxyhemoglobin, and/or oxyhemoglobin, lipids composition, collagen composition, lymphatics and/or lymphamatics, oxygen saturation, water composition, extracellular matrix, and vasculature configuration and/or sprouting. In an example, light which has been transmitted through breast tissue and received by light receivers can be analyzed to identify the presence, composition, shape, size, and/or location of abnormal tissue in the breast based on analysis of changes in one or more of the following biometric markers: hemoglobin, deoxyhemoglobin, and/or oxyhemoglobin, lipids composition, collagen composition, lymphatics and/or lymphamatics, oxygen saturation, water composition, extracellular matrix, and vasculature configuration and/or sprouting.

In an example, a smart bra can activate different pairs of light emitters and light receivers to record spectral changes in light transmitted through the breast tissue along different three-dimensional vectors. Joint analysis of the spectral changes of light beams traveling through the breast tissue along different three-dimensional vectors can identify whether there is abnormal tissue within the breast and, if so, where the abnormal tissue is located. Although light energy is significantly diffused through the depth of breast tissue, joint three-dimensional analysis of light transmitted through multiple intersecting vectors between multiple pairs of light emitters and light receivers can increase the accuracy and locational precision of spectroscopic analysis in order to identify and locate abnormal tissue.

In an example, light which has been transmitted through breast tissue and received by light receivers can be analyzed using: Time Reversal Optical Tomography (TROT), changes in the frequency spectrum of light transmitted through a breast, diffuse optical imaging, Diffuse Optical Tomography (DOT), spectroscopic analysis, analysis of absorption and/or scattering of light transmitted through a breast, near-infrared spectroscopy, changes in the intensity or amplitude of light transmitted through a breast, changes in the phase of light transmitted through a breast, Diffuse Correlation Spectroscopy (DCS), Carlavian Curve Analysis (CCA), machine learning, a neural network, broadband spectroscopy, and/or changes in the spectral distribution of light transmitted through a breast. In an example, spectroscopic analysis of light transmitted through breast tissue can detect spectral troughs caused by absorption of light by unusual concentrations of collagen, hemoglobin, deoxyhemoglobin, oxyhemoglobin, lipids, and/or oxygen.

In an example, light which has been transmitted through breast tissue and received by light receivers can be analyzed to: create an image (e.g. scan or map) which variation in breast tissue density; identify the location of abnormal breast tissue; create an image (e.g. scan or map) which shows abnormal tissue within a breast; identify the molecular and/or cellular composition of the breast; identify the presence of abnormal breast tissue; identify the shape of abnormal breast tissue; create an image (e.g. scan or map) which shows the size of abnormal tissue within a breast; identify the structure of abnormal breast tissue; create an image (e.g. scan or map) which shows the structure of abnormal tissue within a breast; create an image (e.g. scan or map) which variation in breast tissue composition; create a three-dimensional image of a breast; create an image (e.g. scan or map) which shows blood flow within a breast; identify the composition of abnormal breast tissue; create an image (e.g. scan or map) which shows metabolic processes within a breast; create an image (e.g. scan or map) which shows the shape of abnormal tissue within a breast; create a two-dimensional image of a breast; and/or create an image (e.g. scan or map) which shows the concentrations of a substance within a breast.

In an example, a first set of light emitters on a cup can emit light at a first frequency and/or wavelength (or in a first spectral range) and a second set of light emitters on the cup can emit light at a second frequency and/or wavelength (or in a second spectral range). In an example, a first set of light emitters can emit light at a first frequency and/or wavelength (or in a first spectral range), a second set of light emitters can emit light at a second frequency and/or wavelength (or in a second spectral range), and a third set of light emitters can emit light at a third frequency and/or wavelength (or in a third spectral range). In an example, a single light emitter can emit light at a frequency and/or wavelength which varies over time. In an example, light emitters can all emit light at the same frequency and/or wavelength (or in the same spectral range).

In an example, light emitters on a cup can emit frequency and/or wavelength modulated light. In an example, light emitters can emit light at a constant frequency and/or wavelength. In an example, a light emitter can emit light with a frequency between 698 and 703 nm. In an example, a light emitter can emit light with a frequency between 916 and 921 nm. In an example, light emitters can emit light at a frequency and/or wavelength which varies over time.

In an example, a first light emitter can emit light with a wavelength in the range of 600 to 800 nm at a first time; a second light emitter can emit light with a wavelength in the range of 800 nm to 1000 nm at a second time; and a third light emitter can emit light with a wavelength in the range of 1000 nm to 1200 nm at a third time. In an example, a first light emitter can emit light with a wavelength in the range of 650 to 750 nm at a first time; a second light emitter can emit light with a wavelength in the range of 750 nm to 850 nm at a second time; and a third light emitter can emit light with a wavelength in the range of 850 nm to 950 nm at a third time.

In an example, a first light emitter can emit light with a wavelength in the range of 600 to 700 nm; a second light emitter can emit light with a wavelength in the range of 700 nm to 800 nm; and a third light emitter can emit light with a wavelength in the range of 800 nm to 900 nm. In an example, a first light emitter can emit light with a wavelength in the range of 600 to 800 nm; a second light emitter can emit light with a wavelength in the range of 800 nm to 1000 nm; and a third light emitter can emit light with a wavelength in the range of 1000 nm to 1200 nm. In an example, a first light emitter can emit light with a wavelength in the range of 600 to 900 nm and a second light emitter can emit light with a wavelength in the range of 900 nm to 1200 nm. In an example, a light emitter can emit light with a frequency between 828 and 833 nm. In an example, a light emitter can emit light with a frequency between 668 and 673 nm. In an example, a light emitter can emit light with a frequency between 688 and 693 nm.

In an example, a light emitter can emit light energy with a wavelength in the range of 600 to 700 nm. In an example, a first light emitter can emit intensity or amplitude modulated light into the breast with a wavelength in the range of 650 to 750 nm; a second light emitter can emit intensity or amplitude modulated light with a wavelength in the range of 750 nm to 850 nm; and a third light emitter can emit intensity or amplitude modulated light with a wavelength in the range of 850 nm to 950 nm.

In an example, a light emitter can emit light energy with a wavelength in the range of 600 nm to 1,000 nm. In an example, a first light emitter can emit light with a wavelength in the range of 650 to 700 nm; a second light emitter can emit light with a wavelength in the range of 700 nm to 750 nm; and a third light emitter can emit light with a wavelength in the range of 750 nm to 800 nm. In an example, a first light emitter can emit light with a wavelength in the range of 650 to 750 nm; a second light emitter can emit light with a wavelength in the range of 750 nm to 850 nm; and a third light emitter can emit light with a wavelength in the range of 850 nm to 950 nm. In an example, a light emitter can emit light with a frequency between 1098 and 1103 nm. In an example, a light emitter can emit light with a frequency between 1501 and 1506 nm. In an example, a light emitter can emit light with a frequency between 748 and 753 nm. In an example, a light emitter can emit light with a frequency between 1698 and 1703 nm.

In an example, a smart bra can comprise a plurality of light emitters which transmit light into breast tissue at angles relative to the breast surface in the range of 45 to 90 degrees. In an example, a smart bra can comprise a plurality of light emitters which transmit light into breast tissue at angles relative to the breast surface in the range of 85 to 95 degrees. In an example, a smart bra can comprise two or more light emitters which are vertically stacked. In an example, a light emitter can emit a radially-rotating beam of light. In an example, light emitters can emit infrared light. In an example, light emitters can emit near-infrared light. In an example, light emitters can emit red light.

In an example, a first set of light emitters in a cup can emit a pulse of light at a first time and a second set of light emitters in the cup can emit a pulse of light at a second time). In an example, a first set of light emitters can emit light at a first intensity or amplitude level (or at a first time) and a second set of light emitters can emit light at a second intensity or amplitude level (or at a second time). In an example, a first set of light emitters can emit light at a first intensity or amplitude level (or at a first time), a second set of light emitters can emit light at a second intensity or amplitude level (or at a second time), and a third set of light emitters can emit light at a third intensity or amplitude level (or at a third time). In an example, light emitters can all emit a pulse of light at the same time. In an example, light emitters can all emit light at the same intensity or amplitude level (or at the same time).

In an example, a first light emitter at a first location can emit (a pulse of) light at a first time and a second light emitter at a second location can emit (a pulse of) light at a second time. In an example, a first light emitter at a first location on a radial spoke of light emitters can emit (a pulse of) light at a first time and a second light emitter at a second location on the radial spoke can emit (a pulse of) light at a second time. In an example, a first light emitter at a first location on a ring of light emitters can emit (a pulse of) light at a first time and a second light emitter at a second location on the ring can emit (a pulse of) light at a second time. In an example, light emitters in a first hextant of a cup can emit (a pulse of) light at a first time and light emitters in a second hextant of the cup can emit (a pulse of) light at a second time.

In an example, light emitters in a first quadrant of a cup can emit (a pulse of) light at a first time and light emitters in a second quadrant of the cup can emit (a pulse of) light at a second time. In an example, light emitters on the right side of a cup can emit (a pulse of) light at a first time and light emitters on the left side of the cup can emit (a pulse of) light at a second time, or vice versa. In an example, light emitters on the top half of a cup can emit (a pulse of) light at a first time and light emitters on the bottom half of the cup can emit (a pulse of) light at a second time, or vice versa. In an example, light emitters one a first of light emitters can emit (a pulse of) light at a first time and light emitters on a second ring of light emitters can emit (a pulse of) light at a second time. In an example, a light emitter can emit light with a frequency between 1798 and 1803 nm. In an example, a light emitter can emit light with a frequency between 848 and 853 nm.

In an example, a first light emitter can emit a pulse of light with a first duration and a second light emitter can emit a pulse of light with a second duration, wherein the second duration is greater than the first duration. In an example, a light emitter can emit a first pulse of light with a first duration followed by a second pulse of light with a second duration, wherein the second duration is greater than the first duration. In an example, a light emitter can emit a first pulse of light with a first duration followed by a second pulse of light with a second duration, wherein the second duration is less than the first duration.

In an example, a first light emitter can emit light along a first vector and a second light emitter can emit along a second vector. In an example, a light emitter can emit light along a first vector at a first time and along a second vector at a second time. In an example, the incidence angles at which light emitters transmit light onto the surface of a breast can vary with distance of the light emitters from the apex of a concave cup. In an example, the incidence angles at which light emitters transmit light onto the surface of a breast can increase with distance of the light emitters from the apex of a concave cup.

In an example, the incidence angles at which light emitters transmit light onto the surface of a breast can decrease with distance of the light emitters from the apex of a concave cup. In an example, a light emitter can be positioned so as to send light toward the centroid of a breast. In an example, a light emitter can send light along a vector which is perpendicular to a breast surface. In an example, a light emitter can send light at a constant angle and/or focal vector. In an example, a light emitter can send light at an angle and/or focal vector which varies over time.

In an example, a first light emitter (or first optical component including a first light emitter) can emit light with a first polarization level or direction and a second light emitter (or second optical component including a second light emitter) can emit light with a second polarization level or direction. In an example, a light emitter (or optical component including a first light emitter) can emit light with a first polarization level or direction at a first time and light with a second polarization level or direction at a second time.

In an example, a first light emitter (or first optical component including a first light emitter) can emit light with a first collimation level or direction and a second light emitter (or second optical component including a second light emitter) can emit light with a second collimation level or direction. In an example, a light emitter (or optical component including a first light emitter) can emit light with a first collimation level or direction at a first time and light with a second collimation level or direction at a second time.

In an example: the surface of an optical component which faces toward the surface of a breast can be in a first virtual plane when the optical component is in the first configuration; the surface of the optical component which faces toward the surface of a breast can be in a second virtual plane when the optical component is in the second configuration; and the first and second virtual planes can be substantially parallel to each other. In an example: the surface of an optical component which faces toward the surface of a breast can be in a first virtual plane when the optical component is in the first configuration; the surface of the optical component which faces toward the surface of a breast can be in a second virtual plane when the optical component is in the second configuration; and the first and second virtual planes can intersect each other at an angle between 2 and 45 degrees.

In an example, the surface of an optical component which faces toward a breast can be substantially parallel with a local region of the interior surface of a cup in the first configuration. In an example, the surface of an optical component which faces toward a breast can protrude and/or extend out from the interior surface of the cup in the second configuration. In an example, the surface of an optical component which faces toward a breast can slide out from an opening in the interior surface of the cup in the second configuration. In an example, the surface of an optical component which faces toward a breast can stretch and/or distend a local portion the interior surface of the cup away from the rest of the interior surface in the second configuration. In an example, the interior surface of a cup can be non-undulating in the first configuration, but locally-undulating in the second configuration.

In an example, an expandable component can be located between an optical component and the exterior surface of a cup on a smart bra. In an example, the interior surface of a cup can be more elastic, stretchable, and/or compliant than the exterior surface of the cup, so that expansion of an expandable component between the interior and exterior surfaces extends the interior surface outward more than it extends the exterior surface outward. In an example, expansion of an expandable component pushes an optical component away from the interior surface of the cup toward the surface of a breast.

In an example, expansion of an expandable component pushes an optical component away from the interior surface of the cup toward the surface of a breast, thereby shrinking a gap between the optical component and the surface of the breast. In an example, expansion of an expandable component pushes an optical component away from the interior surface of the cup, thereby increasing the pressure level between the optical component and breast tissue. In an example, expansion of an expandable component pushes an optical component away from the interior surface of the cup toward the surface of a breast, thereby improving optical communication between the optical component and breast tissue.

In an example, an expandable component can be an air (or other gas) bladder, compartment, and/or microballoon. In an example, an expandable component can be an air bladder, compartment, and/or microballoon which is located between an optical component and the exterior surface of a cup on a smart bra. In an example, there can be an expandable component for each optical component. In an example, expandable components can be individually, selectively, and differentially inflated so as to individually, selectively, and differentially move selected optical components closer to a breast surface. This enables custom fitting of optical components to the particular shape of a specific breast to minimize optical scanning errors due to gaps between optical components and the surface of the breast. In an example, a smart bra can have a micropneumatic system which moves optical components into closer conformity with the shape of a breast.

In an example, an expandable component can be a bladder or compartment which contains a liquid. In an example, each expandable component can be in fluid communication with a fluid pump through a separate fluid tube or channel between the fluid pump and the expandable component. Alternatively, some or all of the expandable components can be connected to a fluid pump by a common fluid tube or channel, but still be expanded differentially due to different size gaps between their respective optical components and the surface of a breast.

In an example, expandable components can have internal pressure levels which are sufficiently high to push optical components into air gaps in areas of the cup where there are air gaps between optical components and the surface of a breast, but not so high that the expandable components cause optical components to press too much onto breast tissue in areas of the cup where there are no air gaps. In an example, the pressure level inside an expandable component can be in the range of 800 to 850 mmHg. In an example, the pressure level inside an expandable component can be in the range of 700 to 950 mmHg. In an example, the pressure level inside an expandable component can be in the range of 15 to 17 mmHg. In an example, the pressure level inside an expandable component can be in the range of 13 to 19 mmHg.

In an example, a smart bra can comprise an array of optical components (e.g. including a light emitter and/or light receiver) and an array of expandable components (e.g. expandable bladders filled with a flowable substance such as a gas or liquid). In an example, optical components and expandable components can be configured in pairs, wherein each pair has an optical component and an expandable component. In an example, each expandable component can independently and selectively change the configuration of an optical component in one or more ways selected from the group consisting of: changing the distance by which an optical component protrudes out from the interior surface of a bra cup; changing the distance between an optical component and the surface of a person's breast; closing an air gap between an optical component and the surface of a person's breast; changing the angle between an optical component and the interior surface of a bra cup; changing the angle between an optical component and the surface of a person's breast; changing the orientation of an optical component relative to the interior surface of a bra cup; and changing the orientation of an optical component relative to the surface of a person's breast.

In an example, a selected subset of expandable components can be expanded in order to move a selected subset of optical components from their first to second configurations. In an example, each expandable component can be in fluid communication with a pump through a separate tube or channel between the pump and an expandable component. Alternatively, some or all of the expandable components can be connected to a pump by a common tube or channel, but still expand differentially due to different size gaps between their respective optical components and the surface of a breast.

In an example, an expandable component can have a shape which is selected from the group consisting of: pancake, disk, ellipsoidal, oblong, oval, toroidal, hemispherical, and spherical. In an example, an expandable component can have a disk shape in a first configuration and an ellipsoidal shape in an expanded second configuration. In an example, an expandable component can have a pleated and/or folded shape, like an accordion or bellows. In an example, an expandable component can have a disk shape in a first configuration and a cylindrical shape in an expanded second configuration. In an example, an expandable component can be substantially parallel to an optical component. In an example, an expandable component can be flexibly attached to an optical component. In an example, an expandable component can be located between an optical component and an exterior layer of a cup on a smart bra.

In an example, an expandable component can have a longitudinal axis and an optical component can have a longitudinal axis. In an example, these longitudinal axes can be substantially parallel to each other. In an example, an expandable component can have a first width in the first configuration, wherein the first width is between 1 mm and 5 mm. In an example, an expandable component can have a second width in the second configuration, wherein the first width is between 2 mm and 10 mm. In an example, the second width can be greater than the first width. In an example, the second width can be at least 25% greater than the first width.

In an example, an expandable component can have a first cross-sectional area in a first plane which is parallel and/or tangential to the exterior surface of a cup. In an example, an optical component which is flexibly attached to the expandable component can have a second cross-sectional area in a second plane which is parallel and/or tangential to the exterior surface of a cup. In an example, the first cross-sectional area can be substantially the same size as (e.g. within 10% of) the second cross-sectional area. In an example, the first cross-sectional area can be larger than the second cross-sectional area. In an example, the first cross-sectional area can be at least 50% larger than the second cross-sectional area. In an example, the second cross-sectional area can be larger than the first cross-sectional area. In an example, the second cross-sectional area can be at least 50% larger than the first cross-sectional area.

A smart bra which enables selective expansion of only a selected subset of expandable components to move a selected subset of optical components (which would not otherwise contact a breast surface) enables better optical scanning of breast tissue than does a device with uniform expansion. Selective expansion of a subset of expandable components closes gaps between optical components and a breast surface where there are gaps in a first configuration, without creating pressure or deformation between optical components and the breast surface where there are no gaps in the first configuration.

In an example, the selection of which expandable components should be expanded can be based on which optical components are associated with errors in optical scanning data, wherein these errors indicate air gaps between those optical components and breast surface. In an example, the selection of which expandable components should be expanded can be based on distance measurement using infrared light reflection. In an example, a smart bra can further comprise an array of pressure sensors. In an example, the selection of which expandable components should be expanded by the device can be based on which optical components are near pressure sensors which indicate no contact with the breast surface.

In an example, a cup can have an array of expandable components and an array of light emitters, wherein expansion of the expandable components moves the light emitters closer to the surface of a breast. In an example, a smart bra can comprise a plurality of adjustable electromagnetic actuators which selectively compel individual light emitters and/or light receivers toward breast tissue. In an example, a smart bra can comprise a plurality of adjustable piezoelectric actuators which selectively compel individual light emitters and/or light receivers toward breast tissue. In an example, a smart bra can comprise a plurality of adjustable pneumatic or hydraulic actuators which selectively compel individual light emitters and/or light receivers toward breast tissue. In an example, a smart bra can comprise a plurality of adjustable springs which selectively compel individual light emitters and/or light receivers toward breast tissue.

A smart bra which enables selective expansion of only a selected subset of expandable components (thereby moving only optical components which are not contacting breast surface) enables better optical scanning and comfort than a device that only enables uniform expansion. Selective expansion of a subset of expandable components closes gaps between optical components and a breast surface where there are gaps in a first configuration, without creating pressure or deformation between optical components and the breast surface where there are no gaps in the first configuration. This is an advantage over devices that only offer uniform expansion. A device that only offers uniform expansion can cause uncomfortable compression and/or pinching of areas of the breast where there are no air gaps when the device is uniformly expanded in an effort to close areas where there are air gaps.

A smart bra which enables selective expansion of only a selected subset of expandable components to move a selected subset of optical components (which would not otherwise contact a breast surface) enables better optical scanning of breast tissue than does a device with uniform expansion. Selective expansion of a subset of expandable components closes gaps between optical components and a breast surface where there are gaps in a first configuration, without creating pressure or deformation between optical components and the breast surface where there are no gaps in the first configuration.

In an example, a smart bra can include an air pump on the back strap of the bra, wherein the air pump is manually operated to inflate one or more expandable components to improve the fit of optical components relative to the contour of a breast. In an example, an air pump can be operated by the person pressing the pump with their hand. Alternatively, an air pump can be automatically operated by an air impeller which is rotated by electromagnetic motor. In an example, a smart bra can further comprise a liquid pump on the back strap of the bra, wherein the liquid pump is manually operated to expand one or more expandable components to improve the fit of optical components on the contour of a breast.

Alternatively, the liquid pump can be automatically operated by an impellor which is rotated by an electromagnetic motor.

In an example, there can be a single tube or channel which delivers flowable material (e.g. a gas or liquid) from a pump to a plurality of expandable components on a cup of a smart bra. In an example, there can be a right-side tube or channel which delivers flowable material (e.g. a gas or liquid) from a pump to a plurality of expandable components on a right cup and a left-side tube or channel which delivers flowable material (e.g. a gas or liquid) from a pump to a plurality of expandable components on a left cup. In an example, there can be a plurality of individual tubes or channels which deliver flowable material (e.g. a gas or liquid) from a pump to a plurality of individual expandable components, respectively, on a cup of a smart bra.

In an example, a tube or channel can deliver flowable material from a pump to an array of expandable components, wherein flows of the substance to individual expandable components are individually-controllable by an array of control valves. In an example, there can be one control valve for each expandable component, enabling selective and differential expansion of individual expandable components. Alternatively, expandable components can be in fluid communication with each other through a common (air or fluid) tube or channel. In an example, expandable components can be in fluid isolation from each other, except for all being in fluid communication with (and air or fluid) pump. In an example, expandable components can be in fluid isolation from each other due to separate air tubes or channels and/or separate flow valves. In an example, there can be between 10 and 100 tubes or channels which individually deliver flowable material (e.g. a gas or liquid) from a pump to an equal number of expandable components on a cup of a smart bra.

In an example, pressure levels within expandable components can be parameters which are adjusted by a smart bra, instead of distances between optical components and the surface of a breast. In an example, a smart bra for spectroscopic scanning of breast tissue to help detect abnormal tissue can comprise: (i) a bra with two cups which is configured to be worn on a person's breasts, wherein an interior surface of a cup faces toward the person's breast and an exterior surface of the cup faces away from the person's breast; (ii) a first optical component on the interior surface of a cup, wherein the first optical component comprises a light emitter which transmits light into the person's breast and/or a light receiver which receives light which has been transmitted (e.g. reflected or side-to-side transmitted) through the person's breast; (iii) a first inflatable component, wherein inflation of the first inflatable component pushes the first optical component toward the surface of the breast, and wherein the first inflatable component has a first internal pressure level in a first configuration and a second internal pressure level in a second configuration; (iv) a second optical component on the interior surface of a cup, wherein the second optical component comprises a light emitter which transmits light into the person's breast and/or a light receiver which receives light which has been transmitted (e.g. reflected or side-to-side transmitted) through the person's breast; and (v) a second inflatable component, wherein inflation of the second inflatable component pushes the second optical component toward the surface of the breast, and wherein the second inflatable component has a third internal pressure level in the first configuration and a fourth internal pressure level in the second configuration. In an example, the fourth internal pressure level can equal the second internal pressure level in the second configuration. In an example, the first and second inflatable components can be selectively and differentially inflated between the first and second configurations in order to bring their internal pressures closer together.

In an example, a smart bra for spectroscopic scanning of breast tissue to help detect abnormal tissue can comprise: a bra with two cups which is configured to be worn on a person's breasts, wherein an interior surface of a cup faces toward the person's breast and an exterior surface of the cup faces away from the person's breast; and an array of optical components on the interior surface of a cup; wherein each optical component further comprises a light emitter which transmits light into the person's breast and an expandable member which pushes the light emitter toward the surface of the person's breast when the expandable member is expanded. In an example, optical components for which there are air gaps between light emitters and the surface of the person's breast can be detected by spectroscopic analysis of light which has been transmitted (e.g. reflected or side-to-side transmitted) from the light emitters through breast tissue. For those optical components for which such air gaps are detected, expandable members attached to those components are expanded until spectroscopic analysis shows that the gaps have been closed.

In an example, a smart bra for spectroscopic scanning of breast tissue to help detect abnormal tissue can comprise an array of optical components on a bra cup, wherein each optical component further comprises: (i) a light emitter which emits light into breast tissue and/or a light receiver which receives light which has been transmitted (e.g. reflected or side-to-side transmitted) through breast tissue; and (ii) an expandable component which moves the light emitter and/or light receiver closer to the surface of a breast when the expandable component is expanded. In an example, the smart bra can detect the subset of optical components for which there are air gaps between light emitters and/or light receivers and the surface of the breast. In an example, expandable components in that subset of optical components are selectively expanded in order to close those air gaps.

In an example, a smart bra for spectroscopic scanning of breast tissue to help detect abnormal tissue can comprise an array of optical components on a bra cup, wherein each optical component further comprises: (i) a light emitter which emits light into breast tissue and/or a light receiver which receives light which has been transmitted (e.g. reflected or side-to-side transmitted) through breast tissue; and (ii) an inflatable component which pushes the light emitter and/or light receiver closer to the surface of a breast when the inflatable component is inflated. In an example, the smart bra can detect the subset of optical components for which there are air gaps between light emitters and/or light receivers and the surface of the breast. In an example, inflatable components in that subset of optical components are selectively inflated in order to close those air gaps.

In an example, a smart bra for spectroscopic scanning of breast tissue to help detect abnormal tissue can comprise an array of optical components on a bra cup, wherein each optical component further comprises: (i) a light emitter which emits light into breast tissue and/or a light receiver which receives light which has been transmitted (e.g. reflected or side-to-side transmitted) through breast tissue; and (ii) an expandable component which moves the light emitter and/or light receiver closer to the surface of a breast when the expandable component is expanded. In an example, the smart bra can detect the subset of optical components for which light emitters and/or light receivers are more than 1 mm from the surface of the breast and only expandable components in that subset are expanded. In an example, the smart bra can detect the subset of optical components for which light emitters and/or light receivers are more than 3 mm from the surface of the breast and only expandable components in that subset are expanded.

In an example, a smart bra for spectroscopic scanning of breast tissue to help detect abnormal tissue can comprise: a bra with two cups which is configured to be worn on a person's breasts, wherein an interior surface of a cup faces toward the person's breast and an exterior surface of the cup faces away from the person's breast; and an array of optical components on the interior surface of a cup; wherein each optical component further comprises: a light emitter which transmits light into the person's breast and/or a light receiver which receives light which has been transmitted (e.g. reflected or side-to-side transmitted) through the person's breast; and an expandable member which pushes the light emitter and/or light receiver toward the surface of the person's breast when the expandable member is expanded. In an example, expansion of expandable members closes gaps between light emitters and/or light receivers and the surface of the person's breast.

In an example, a smart bra for spectroscopic scanning of breast tissue to help detect abnormal tissue can comprise: a bra with two cups which is configured to be worn on a person's breasts, wherein an interior surface of a cup faces toward the person's breast and an exterior surface of the cup faces away from the person's breast; and an array of optical components on the interior surface of a cup; wherein each optical component further comprises (i) a light emitter which transmits light into the person's breast and/or a light receiver which receives light which has been transmitted (e.g. reflected or side-to-side transmitted) through the person's breast and (ii) an inflatable member which pushes the light emitter and/or light receiver toward the surface of the person's breast when the inflatable member is expanded; and an air pump which is in fluid communication with the inflatable members. In an example, inflation of inflatable members with air from the air pump closes gaps between the light emitters and/or light receivers and the surface of the person's breast.

In an example, a smart bra for spectroscopic scanning of breast tissue to help detect abnormal tissue can comprise: a bra with two cups which is configured to be worn on a person's breasts, wherein an interior surface of a cup faces toward the person's breast and an exterior surface of the cup faces away from the person's breast; and an array of optical components on the interior surface of a cup; wherein each optical component further comprises a light emitter which transmits light into the person's breast and an inflatable bladder which pushes the light emitter toward the surface of the person's breast when the inflatable bladder is inflated. In an example, optical components for which there are air gaps between light emitters and the surface of the person's breast can be detected by spectroscopic analysis of light which has been transmitted (e.g. reflected or side-to-side transmitted) from the light emitters through breast tissue. For optical components for which such air gaps are detected, inflatable bladders in those components are inflated until spectroscopic analysis shows that the gaps have been closed.

In an example, a smart bra for spectroscopic scanning of breast tissue to help detect abnormal tissue can comprise: a bra with two cups which is configured to be worn on a person's breasts, wherein an interior surface of a cup faces toward the person's breast and an exterior surface of the cup faces away from the person's breast; and an array of optical components on the interior surface of a cup; wherein each optical component further comprises a light emitter which transmits light into the person's breast and an inflatable bladder which pushes the light emitter toward the surface of the person's breast when the inflatable bladder is inflated; wherein a subset of the array of optical components is identified for which there are air gaps between the light emitters and the surface of the person's breast; wherein inflatable bladders in the subset of the array of optical components are inflated in order to close those air gaps. In an example, inflatable bladders in the array of optical components which are not part of the subset are not inflated (or not inflated as much).

In an example, a smart bra for spectroscopic scanning of breast tissue to help detect abnormal tissue can comprise: a bra with two cups which is configured to be worn on a person's breasts, wherein an interior surface of a cup faces toward the person's breast and an exterior surface of the cup faces away from the person's breast; and an array of optical components on the interior surface of a cup; wherein each optical component further comprises a light emitter which transmits light into the person's breast, a light receiver which receives light which has been transmitted (e.g. reflected or side-to-side transmitted) through the person's breast, and an inflatable bladder which pushes the light emitter and light receiver toward the surface of the person's breast when the inflatable bladder is inflated; wherein a subset of the array of optical components is identified for which there are air gaps between the light emitters and light receivers and the surface of the person's breast; wherein inflatable bladders in the subset of the array of optical components are selectively inflated in order to selectively close the air gaps. In an example, inflatable bladders in the array of optical components which are not part of the subset are not inflated (or not inflated as much).

In an example, a smart bra for spectroscopic scanning of breast tissue to help detect abnormal tissue can comprise: (i) a bra with two cups which is configured to be worn on a person's breasts, wherein an interior surface of a cup faces toward the person's breast and an exterior surface of the cup faces away from the person's breast; (ii) an array of optical components on the interior surface of a cup, wherein each optical component further comprises a light emitter which transmits light into the person's breast and/or a light receiver which receives light which has been transmitted (e.g. reflected or side-to-side transmitted) through breast tissue; and (iii) an array of inflatable members (e.g. air bladders), wherein the inflatable members selectively change the configurations of one or more optical components in the array of optical components in one or more ways selected from the group consisting of: changing the distances by which one or more optical components protrude from the interior surface of a bra cup; changing the distances between one or more optical components and the surface of the person's breast; closing air gaps between one or more optical components and the surface of the person's breast; changing the angles between one or more optical components and the interior surface of a bra cup; changing the angles between one or more optical components and the surface of the person's breast; changing the orientations of one or more optical components relative to the interior surface of a bra cup; and changing the orientations of one or more optical components relative to the surface of the person's breast.

In an example, a smart bra for spectroscopic scanning of breast tissue to help detect abnormal tissue can comprise: (i) a bra with two cups which is configured to be worn on a person's breasts, wherein an interior surface of a cup faces toward the person's breast and an exterior surface of the cup faces away from the person's breast; (ii) a first optical component on the interior surface of a cup, wherein the first optical component comprises a light emitter which transmits light into the person's breast and/or a light receiver which receives light which has been transmitted (e.g. reflected or side-to-side transmitted) through the person's breast, and wherein there is an air gap between the first optical component and the surface of the person's breast in a first configuration and no air gap between the first optical component and the surface of the person's breast in a second configuration; (iii) a first expandable component, wherein expansion of the first expandable component moves the first optical component from the first configuration to the second configuration; (iv) a second optical component on the interior surface of a cup, wherein the second optical component comprises a light emitter which transmits light into the person's breast and/or a light receiver which receives light which has been transmitted (e.g. reflected or side-to-side transmitted) through the person's breast, and wherein there is an air gap between the second optical component and the surface of the person's breast in the first configuration and no air gap between the second optical component and the surface of the person's breast in the second configuration; and (v) a second expandable component, wherein expansion of the second expandable component moves the second optical component from the first configuration to the second configuration.

In an example, a smart bra for spectroscopic scanning of breast tissue to help detect abnormal tissue can comprise: (i) a bra with two cups which is configured to be worn on a person's breasts, wherein an interior surface of a cup faces toward the person's breast and an exterior surface of the cup faces away from the person's breast; (ii) a first optical component on the interior surface of a cup, wherein the first optical component comprises a light emitter which transmits light into the person's breast and/or a light receiver which receives light which has been transmitted (e.g. reflected or side-to-side transmitted) through the person's breast; (iii) a first expandable component, wherein expansion of the first expandable component moves the first optical component; (iv) a second optical component on the interior surface of a cup, wherein the second optical component comprises a light emitter which transmits light into the person's breast and/or a light receiver which receives light which has been transmitted (e.g. reflected or side-to-side transmitted) through the person's breast; and (v) a second expandable component, wherein expansion of the second expandable component moves the second optical component, and wherein the first expandable component and the second expandable component can be moved independently from each other.

In an example, a smart bra for spectroscopic scanning of breast tissue to help detect abnormal tissue can comprise: (i) a bra with two cups which is configured to be worn on a person's breasts, wherein an interior surface of a cup faces toward the person's breast and an exterior surface of the cup faces away from the person's breast; (ii) a first optical component on the interior surface of a cup, wherein the first optical component comprises a light emitter which transmits light into the person's breast and/or a light receiver which receives light which has been transmitted (e.g. reflected or side-to-side transmitted) through the person's breast; (iii) a first inflatable component, wherein inflation of the first inflatable component moves the first optical component; (iv) a second optical component on the interior surface of a cup, wherein the second optical component comprises a light emitter which transmits light into the person's breast and/or a light receiver which receives light which has been transmitted (e.g. reflected or side-to-side transmitted) through the person's breast; and (v) a second inflatable component, wherein inflation of the second inflatable component moves the second optical component, and wherein the first inflatable component and the second inflatable component can be inflated independently from each other.

In an example, a smart bra for spectroscopic scanning of breast tissue to help detect abnormal tissue can comprise: (i) a bra with two cups which is configured to be worn on a person's breasts, wherein an interior surface of a cup faces toward the person's breast, and wherein an exterior surface of the cup faces away from the person's breast; (ii) a first optical component on the interior surface of a cup, wherein the first optical component comprises a light emitter which transmits light into the person's breast and/or a light receiver which receives light which has been transmitted (e.g. reflected or side-to-side transmitted) through the person's breast, and wherein there is an air gap between the first optical component and the surface of the person's breast in a first bra configuration and no air gap between the first optical component and the surface of the person's breast in a second bra configuration; (iii) a first expandable component whose expansion moves the first optical component, wherein expansion of the first expandable component moves the first optical component from the first bra configuration to the second bra configuration; (iv) a second optical component on the interior surface of a cup, wherein the second optical component comprises a light emitter which transmits light into the person's breast and/or a light receiver which receives light which has been transmitted (e.g. reflected or side-to-side transmitted) through the person's breast, and wherein there is no air gap between the second optical component and the surface of the person's breast in either the first bra configuration or the second bra configuration; and (v) a second expandable component whose expansion moves the second component, wherein the second expandable component does not move from the first bra configuration to the second bra configuration.

In an example, a smart bra for spectroscopic scanning of breast tissue to help detect abnormal tissue can comprise: a smart bra with two cups which are configured to be worn on a person's breasts; wherein a cup has an internal layer which is closest to the surface of the person's breast, an external layer which is farthest from the surface of the person's breast, and a middle layer between the first internal layer and the external layer; wherein the internal layer is transparent and is made from a material with a first Shore 00 value; wherein the middle layer is compressible and contains light emitters and light receivers; wherein the exterior layer is opaque and is made from a material with a second Shore 00 value; and wherein the second Shore 00 value is greater than the Shore 00 value. In an example, the first Shore 00 value can be less than 5 and the second Shore 00 value can be greater than 5. In an example, the first Shore 00 value can be less than 20 and the second Shore can be value is greater than 20.

In an example, a smart bra for spectroscopic scanning of breast tissue to help detect abnormal tissue can comprise: a smart bra with two cups which are configured to be worn on a person's breasts; wherein a cup has an internal layer which is closest to the surface of the person's breast, an external layer which is farthest from the surface of the person's breast, and a middle layer between the first internal layer and the external layer; wherein the internal layer is transparent and has a first level of flexibility and/or elasticity; wherein the middle layer is compressible and contains light emitters and light receivers; wherein the exterior layer is opaque and has a second level of flexibility and/or elasticity; and wherein the second level is less than the first level.

In an example, a smart bra for spectroscopic scanning of breast tissue to help detect abnormal tissue can comprise: a smart bra with two cups which are configured to be worn on a person's breasts; wherein a cup has an internal layer which is closest to the surface of the person's breast, an external layer which is farthest from the surface of the person's breast, and a middle layer between the first internal layer and the external layer; wherein the internal layer is transparent and has a first durometer level; wherein the middle layer is compressible and contains light emitters and light receivers; wherein the exterior layer is opaque and has a second durometer level; and wherein the second level is greater than the first level.

In an example, a smart bra can have a cup with a star-burst array of light emitters and/or light receivers. In an example, a cup can be divided into two halves around a central apex, wherein light from light emitters in a first half is received by light receivers in second (e.g. opposite) half. In an example, a smart bra can have a cup with a hexagonal mesh (or grid)

with a plurality of light emitters located at a first set of mesh (or grid) vertexes and a plurality of light receivers located at a second set of mesh (or grid) vertexes. In an example, a smart bra can have a cup with a latitude-and-longitude mesh (or lattice) of light emitters and/or light receivers. In an example, a smart bra can have a cup with a rows-and-columns array of light emitters and/or light receivers. In an example, a cup can be divided into four quadrants around a central apex, wherein light from light emitters in a first quadrant is received by light receivers in second (e.g. opposite) quadrant. In an example, a cup can have a transparent polydimethylsiloxane (PDMS) layer.

In an example, a smart bra can have a cup with one or more strands of elastic miniature rope lighting with a plurality of light emitters. In an example, a cup can have an interior layer made from polydimethylsiloxane (PDMS). In an example, a smart bra can have a cup with a hexagonal mesh (or grid) with a plurality of light emitters and/or light receivers located at mesh (or grid) vertexes. In an example, a cup can be divided into six hextants around a central apex, wherein light from light emitters in a first hextant is received by light receivers in second (e.g. opposite) hextant. In an example, a smart bra can have a cup with a hexagonal mesh (or grid) with a plurality of light emitters and/or light receivers.

In an example, a cup can have a grid or mesh of light emitters and/or light receivers. In an example, a grid or mesh can be less dense (e.g. having elements farther apart) toward the center of a cup than toward the periphery of a cup. In an example, a grid or mesh can be more dense (e.g. having elements closer together) toward the center of a cup than toward the periphery of a cup. In an example, a grid or mesh can have hexagonal cells. In an example, a grid or mesh can have hexagonal openings or gaps. In an example, a grid or mesh can be a honeycomb grid or mesh. In an example, a grid or mesh can have quadrilateral cells. In an example, a grid or mesh can have quadrilateral openings or gaps.

In an example, a cup on a smart bra can have an elastic interior layer. In an example, there can be opaque polymer rings around light emitters on the interior of a cup. In an example, a cup on a smart bra can have an opaque exterior layer (facing away the breast) in order to: reduce penetration of light from the environment into the cup; and reduce the escape of light from light emitters out of the cup. In an example, there can be holes, pockets, and/or openings in the middle layer of a cup which hold optical components such as light emitters or light receivers. In an example, a cup on a smart bra can have a transparent interior layer which covers light emitters and light receivers. In an example, a middle layer of a cup can soft and compressible.

In an example, there can be opaque polygonal light shields around light emitters on the interior of a cup. In an example, there can be opaque rings around light emitters on the interior of a cup. In an example, a cup on a smart bra can have a transparent interior layer. In an example, there can be holes, pockets, and/or openings in the middle layer of a cup which hold expandable components such as fluid bladders or electromagnetic actuators. In an example, there can be opaque circular light shields around light emitters on the interior of a cup. In an example, there can be opaque elastomeric polymer rings around light emitters on the interior of a cup. In an example, a cup on a smart bra can have a soft and compressible middle layer, between an interior layer which faces the breast and an exterior layer which faces away from the breast.

In an example, a smart bra can comprise a cup with an array of light emitters and light receivers which are distributed along the lower perimeter of the cup spanning the 3 o'clock and 9 o'clock locations on the perimeter. In an example, a smart bra can comprise a cup with an array of matched pairs of light emitters and light receivers which is distributed around between 45% and 75% of the (base) perimeter of the cup. In an example, a smart bra can comprise a cup with an array of light emitters and light receivers which are distributed along the lower perimeter of the cup between the 3 o'clock and 9 o'clock locations on the perimeter. In an example, a smart bra can comprise a cup with an array of light emitters and light receivers which are distributed along the lower perimeter of the cup spanning the 4 o'clock and 8 o'clock locations on the perimeter.

In an example, a smart bra can comprise a cup with an array of light emitters and light receivers which are distributed along the lower perimeter of the cup spanning the 5 o'clock and 7 o'clock locations on the perimeter. In an example, a smart bra can comprise a cup with an array of matched pairs of light emitters and light receivers which is distributed around between 25% and 50% of the (base) perimeter of the cup. In an example, a smart bra can comprise a cup with an array of light emitters and light receivers which are distributed along the lower perimeter of the cup between the 4 o'clock and 8 o'clock locations on the perimeter. In an example, a smart bra can comprise a cup with an array of matched pairs of light emitters and light receivers which is distributed around at least 50% of the (base) perimeter of the cup.

In an example, a smart bra can comprise a cup with an array of light receivers which receive light after it has been transmitted through breast tissue. The term "transmitted" as used herein with respect to light includes light which has been reflected back from a relatively-shallow layer of breast tissue as well as light which has been transmitted from one surface (e.g. the right side) of a breast to another surface (e.g. the left side) of the breast. In both cases, light has been transmitted through breast tissue to some extent. This inclusive definition of transmitted light is used herein because there are definitional problems in trying to otherwise distinguish between reflected and transmitted light when it comes to optical scanning of the breast. If one were to try to distinguish between reflected and transmitted light based on tissue depth, then how far below the outermost skin layer would light have to penetrate before light is called transmitted rather than reflected—1 nm? 1 mm? 5 mm? 10 mm? 50 mm?

In an example, a smart bra can have light emitters and/or light receivers which are arranged rings on the interior of a cup, wherein the light emitters transmit light into breast tissue and the light receivers receive light which has been transmitted (e.g. reflected or side-to-side transmitted) through the breast tissue. In an example, rings of light emitters and/or light receivers can be on an interior layer of a multi-layer cup. In an example, rings of light emitters and/or light receivers can be circular, elliptical, oval, egg, or cardioid shaped rings. In an example, rings of light emitters and/or light receivers can be nested (e.g. concentric) rings. In an example, rings of light emitters and/or light receivers can encircle the apex of a concave cup. In an example, rings of light emitters and/or light receivers can be around the chest-wall-facing perimeter of a cup.

In an example, a cup can have a half ring of light emitters and/or light receivers around at half of the perimeter of the cup. In an example, light emitters and/or light receivers on a cup can be configured on (sinusoidal) rings with four undulations and/or phases. In an example, proximal pairs of light emitters on a ring can be separated by 90 degrees around the ring. In an example, a first ring on a cup can have only light emitters and a second ring on the cup can have only light receivers. In an example, light emitters and/or light receivers on a cup can be configured on (sinusoidal) rings with ten or more undulations and/or phases. In an example, proximal pairs of light receivers on a ring can be separated by 30 degrees around the ring.

In an example, a smart bra can comprise at least ten nested elastic rings in a cup, wherein each ring includes: elastic material, an undulating electroconductive channel (such as a sinusoidal wire or conductive thread), and a plurality of light emitters which are powered by the electroconductive channel. In an example, light emitters can be on one quadrant of a ring and light receivers can be on the opposite quadrant of the ring. In an example, proximal pairs of light receivers on rings which are closer to the apex of a cup can be closer together than those on rings which are farther from the apex of the cup. In an example, a smart bra can comprise six nested elastic rings in a cup, wherein each ring includes elastic material, an undulating electroconductive channel (such as a sinusoidal wire or conductive thread), and a plurality of light emitters which are powered by the electroconductive channel. In an example, light receivers on a ring can be equidistant. In an example, there can be a greater number of light emitters than light receivers in a ring.

In an example, a smart bra can comprise eight nested elastic rings in a cup, wherein each ring includes: elastic material, an undulating electroconductive channel (such as a sinusoidal wire or conductive thread), and a plurality of light receivers which are powered by the electroconductive channel. In an example, light emitters on a ring can be activated in a clockwise (or counter-clockwise) sequence. In an example, rings which are closer to the apex of a concave cup can have more light emitters than rings which are farther from the apex of the cup. In an example, light emitters and/or light receivers can be arranged on the interior of a cup in undulating (e.g. sinusoidal) circular, elliptical, oval, egg, or cardioid shaped rings.

In an example, a smart bra can comprise elastic circular, elliptical, oval, egg, or cardioid shaped rings with light emitters and/or light receivers. In an example, light emitters on a ring can be equidistant. In an example, rings which are closer to the apex of a concave cup can have more light receivers than rings which are farther from the apex of the cup. In an example, a ring on a cup can include light emitters and/or light receivers which are connected by conductive thread or yarn. In an example, light emitters and/or light receivers on rings which are closer to the center of the cup can be farther apart than those on rings which are farther from the center of the cup. In an example, proximal pairs of light receivers on a ring can be separated by 45 degrees around the ring. In an example, a ring on a cup can include light emitters and/or light receivers which are connected by an undulating (e.g. sinusoidal) wire. In an example, light emitters around a ring can be configured in a sequence of different frequencies, such as alternating between emitters which emit light with a first frequency and emitters which emit light with a second frequency. In an example, proximal pairs of light receivers on a ring can be separated by 90 degrees around the ring.

In an example, a smart bra can comprise six nested elastic rings in a cup, wherein each ring includes elastic material, an undulating electroconductive channel (such as a sinusoidal wire or conductive thread), and a plurality of light receivers which are powered by the electroconductive channel. In an example, light receivers on rings which are closer to the apex of a cup can be closer together than those on rings which are farther from the apex of the cup. In an example, there can be a greater number of light receivers than light emitters in a ring. In an example, a smart bra can have electroconductive rings which are sewn into a cup, wherein these rings are connected to an array of light emitters and light receivers on the interior of the cup.

In an example, a smart bra can have nested (e.g. concentric) electroconductive rings which are sewn into a cup, wherein these rings are connected to an array of light emitters and light receivers on the interior of the cup. In an example, nested rings of light emitters and/or light receivers in a cup can be different shapes as well as different sizes. In an example, there can be an alternating sequence of rings of only light emitters and rings of only light receivers as one moves away from the apex of a concave cup.

In an example, light emitters and/or light receivers can be arranged on the interior of a cup in circular, elliptical, oval, egg, or cardioid shaped rings. In an example, proximal pairs of light emitters on a ring can be equidistant. In an example, a cup can have a ring of light emitters and/or light receivers around the entire perimeter of the cup. In an example, light emitters and/or light receivers on a cup can be configured on (sinusoidal) rings with six undulations and/or phases. In an example, proximal pairs of light emitters on rings which are closer to the apex of a cup can be closer together than those on rings which are farther from the apex of the cup. In an example, a smart bra can have; a convex polar coordinate (e.g. spoke and ring) array of light emitters and/or light receivers. In an example, proximal pairs light emitters on rings which are closer to the apex of a cup can be farther apart than those on rings which are farther from the apex of the cup.

In an example, light emitters can be on one side of a ring and light receivers can be on the opposite side of the ring. In an example, rings can have an alternating sequence of light emitters and light detectors around the circumference of the ring. In an example, a smart bra can comprise eight nested elastic rings in a cup, wherein each ring includes: elastic material, an undulating electroconductive channel (such as a sinusoidal wire or conductive thread), and a plurality of light emitters which are powered by the electroconductive channel. In an example, light emitters in one ring can emit light with a first frequency (or in a first spectral range) and light emitters in a second ring can emit light with a second frequency (or in a second spectral range). In an example, rings of light emitters and/or light receivers in a cup can be nested, but not concentric.

In an example, light emitters on rings which are closer to the apex of a cup can be closer together than those on rings which are farther from the apex of the cup. In an example, rings which are farther from the apex of a concave cup can have more light emitters than rings which are closer to the apex of the cup. In an example, a cup can have light emitters and light receivers which are arranged in a hub-and-spoke configuration. In an example, light emitters and/or light receivers on a cup can be configured on (sinusoidal) rings with eight undulations and/or phases. In an example, proximal pairs of light receivers on a ring can be equidistant. In an example, a smart bra can comprise elastic rings in a cup, wherein each ring includes elastic material, an undulating electroconductive channel (such as a sinusoidal wire or conductive thread), and a plurality of light receivers which are powered by the electroconductive channel.

In an example, light emitters on rings which are closer to the apex of a cup can be farther apart than those on rings which are farther from the apex of the cup. In an example, rings which are farther from the apex of a concave cup can have more light receivers than rings which are closer to the apex of the cup. In an example, a smart bra can comprise four nested elastic rings in a cup, wherein each ring includes elastic material, an undulating electroconductive channel (such as a sinusoidal wire or conductive thread), and a plurality of light emitters which are powered by the electroconductive channel.

In an example, light emitters on rings which are closer to the apex of a cup can direct light into breast tissue at an incidence angle which is closer to 90 degrees than light emitters on rings which are farther from the apex of the cup. In an example, the number of rings of light emitters can be greater than the number of rings of light receivers. In an example, a smart bra can comprise four nested elastic rings in a cup, wherein each ring includes elastic material, an undulating electroconductive channel (such as a sinusoidal wire or conductive thread), and a plurality of light receivers which are powered by the electroconductive channel. In an example, light emitters on rings which are farther from the apex of a cup can direct light into breast tissue at an incidence angle which is closer to 90 degrees than light emitters on rings which are closer to the apex of the cup. In an example, the number of rings of light emitters can be less than the number of rings of light receivers.

In an example, light receivers on rings which are closer to the apex of a cup can be farther apart than those on rings which are farther from the apex of the cup. In an example, there can be alternating rings of light emitters and light receivers as one moves outward from the center of a cup. In an example, light emitters and/or light receivers can be distributed around undulating (e.g. sinusoidal) rings on the interior of a cup. In an example, proximal pairs of light emitters on a ring can be separated by 60 degrees around the ring. In an example, light emitters and/or light receivers can be configured on undulating (e.g. sinusoidal) rings on the interior of a cup. In an example, proximal pairs of light emitters on a ring can be separated by 45 degrees around the ring. In an example, a smart bra can comprise at least ten nested elastic rings in a cup, wherein each ring includes: elastic material, an undulating electroconductive channel (such as a sinusoidal wire or conductive thread), and a plurality of light receivers which are powered by the electroconductive channel.

In an example, proximal pairs of light emitters on a ring can be separated by 30 degrees around the ring. In an example, arrays of nested rings of light emitters and/or light receivers can be asymmetric with respect to the apex of a concave cup. In an example, proximal pairs light receivers on rings which are closer to the apex of a cup can be farther apart than those on rings which are farther from the apex of the cup. In an example, there can be an equal number of rings of light emitters and light receivers on a ring. In an example, a smart bra can comprise elastic rings in a cup, wherein each ring includes elastic material, an undulating electroconductive channel (such as a sinusoidal wire or conductive thread), and a plurality of light emitters which are powered by the electroconductive channel.

In an example, there can be an alternating sequence of rings of only light emitters and rings of only light receivers as one moves toward the apex of a concave cup. In an example, a ring on a cup can include light emitters and/or light receivers which are connected by an elastomeric (silicone-based) polymer which has been coated, impregnated, or doped with conductive particles. In an example, light emitters and/or light receivers on rings which are closer to the center of the cup can be closer together than those on rings which are farther from the center of the cup. In an example, proximal pairs of light receivers on a ring can be separated by 60 degrees around the ring. Relevant variations discussed elsewhere in this disclosure or in priority-linked disclosures can also be applied to these figures and examples.

FIGS. 3 and 4 show views, at two different times, of a smart bra for spectroscopic scanning of breast tissue to help detect abnormal tissue. This example is similar to the one shown in FIGS. 1 and 2, except that expandable components are electromagnetic actuators instead of gas-filled or liquid-filled bladders. FIG. 3 shows this smart bra at a first time, before it has been adjusted to close any air gaps between optical scanning components and the surface of a breast for more accurate spectroscopic scanning. FIG. 4 shows this smart bra at a second time, after it has been adjusted to close any air gaps between optical scanning components and the surfaces of the breast. The upper portions of FIGS. 3 and 4 show opaque frontal views of the smart bra. Dotted-line ellipses in the lower portions of FIGS. 3 and 4 show cross-sectional close-up views of optical components, a lower portion of the breast, and air gaps between some of the optical components and the surface of the breast. These air gaps are closed by the device in FIG. 4.

The smart bra shown in FIGS. 3 and 4 can be described as a smart bra for spectroscopic scanning of breast tissue to help detect abnormal tissue which comprises: (i) a bra with two cups which is configured to be worn on a person's breasts, wherein an interior surface of a cup faces toward the person's breast and an exterior surface of the cup faces away from the person's breast; (ii) a first optical component on the interior surface of a cup, wherein the first optical component comprises a light emitter which transmits light into the person's breast and/or a light receiver which receives light which has been transmitted (e.g. reflected or side-to-side transmitted) through the person's breast, wherein the first optical component is a first distance from the surface of the person's breast in a first configuration and a second distance from the surface of the person's breast in a second configuration, and wherein a first distance adjustment is the first distance minus the second distance; (iii) a first electromagnetic expandable component, wherein expansion of the first electromagnetic expandable component moves the first optical component from the first configuration to the second configuration; (iv) a second optical component on the interior surface of the cup, wherein the second optical component comprises a light emitter which transmits light into the person's breast and/or a light receiver which receives light which has been transmitted (e.g. reflected or side-to-side transmitted) through the person's breast, wherein the second optical component is a third distance from the surface of the person's breast in the first configuration and a fourth distance from the surface of the person's breast in the second configuration, wherein a second distance adjustment is the third distance minus the fourth distance, and wherein the second distance adjustment is greater than the first distance adjustment; and (v) a second electromagnetic expandable component, wherein expansion of the second electromagnetic expandable component moves the second optical component from the first configuration to the second configuration.

With respect to specific components, the smart bra shown in FIGS. 3 and 4 comprises: (i) a bra 301 with two cups which is configured to be worn on a person's breasts, wherein an interior surface of a cup faces toward the person's breast 310, and wherein an exterior surface 302 of the cup faces away from the person's breast; (ii) a first optical component on the interior surface of a cup, wherein the first optical component comprises a light emitter 307 which transmits light into the person's breast and a light receiver 309 which receives light which has been transmitted (e.g. reflected or side-to-side transmitted) through the person's breast, wherein the first optical component is a first distance from the surface of the person's breast in a first configuration (shown in FIG. 3) and a second distance from the surface of the person's breast in a second configuration (shown in FIG. 4), and wherein a first distance adjustment is the first distance minus the second distance; (iii) a first electromagnetic expandable component 308, wherein expansion of the first electromagnetic expandable component moves the first optical component from the first configuration to the second configuration; (iv) a second optical component on the interior surface of the cup, wherein the second optical component comprises a light emitter 303 which transmits light into the person's breast and a light receiver 305 which receives light which has been transmitted (e.g. reflected or side-to-side transmitted) through the person's breast, wherein the second optical component is a third distance from the surface of the person's breast in the first configuration (shown in FIG. 3) and a fourth distance from the surface of the person's breast in the second configuration (shown in FIG. 4), wherein a second distance adjustment is the third distance minus the fourth distance, and wherein the second distance adjustment is greater than the first distance adjustment; and (v) a second electromagnetic expandable component 304, wherein expansion of the second electromagnetic expandable component moves the second optical component from the first configuration to the second configuration.

In the smart bra shown in FIGS. 3 and 4, expandable components 308 and 304 are electromagnetic actuators (such as electromagnetic motors, electromagnets, or solenoids) which are activated by the transmission of electricity through wire 306. In an example, this smart bra can further comprise a battery on the back strap which transmits electricity through the wire to the electromagnetic actuators. In an example, this smart bra can further comprise a data processor which controls selective transmission of electricity to a subset of expandable components connected to only those optical components for which there are air gaps between those components and the surface of the person's breast.

In FIG. 3, a first optical component (including light emitter 307 and light receiver 309) has close contact with the surface of breast tissue 310, but there is an air gap between a second optical component (including light emitter 303 and light receiver 305) and breast tissue. This air gap can cause errors in optical scanning of breast tissue. In FIG. 4, the second expandable component 304 has been selectively expanded by the device, thereby pushing the second optical component closer to the surface of the breast tissue. This closes the air gap and reduced errors in optical scanning Differential expansion of the second expandable component relative to the first expandable component helps the smart bra to better conform to the shape of the breast, reducing air gaps and improving the quality of optical scanning, without expanding other areas of the cup which could cause tightness or discomfort.

In an example, a smart bra can be made and sold in standard bra sizes (e.g. standard chest and cup sizes). In an example, a smart bra can be made with a stretchable, elastic, flexible, and/or conforming material (e.g. stretchable, elastic, flexible, and/or conforming fabric). In an example, a smart bra can have optical components on both cups in order to optically scan both breasts. In an example, results from optical scanning of right and left breasts can be compared and/or contrasted to help detect abnormal breast tissue. Also, results from more recent scans can be compared and/or contrasted with earlier scans to help detect growth of abnormal breast tissue.

In an example, an optical component can further comprise one or more components selected from the group consisting of: a mirror; a micromirror array; a lens; an optical filter, and a prism. In an example, a smart bra can comprise additional electronic and mechanical components which are located on the back strap of the bra. These additional electronic and mechanical components can be selected from the group consisting of: a battery; a data processor; a memory; a wireless data transmitter; and a wireless data receiver. In an example, a light emitter can emit light with a frequency between 903 and 908 nm.

In an example, a smart bra can be worn on a periodic (e.g. annual, monthly, weekly, or daily) basis in order to obtain a periodic longitudinal time series of optical of breast tissue for identification of possible changes in tissue composition. In an example, a smart bra can be worn as a regular undergarment during everyday life for relatively-continuous monitoring for early identification of possible changes in tissue composition. In an example, data from light receivers in a smart bra can be transmitted to a separate data processor for spectroscopic analysis to identify changes in breast tissue composition and/or help identify abnormal breast tissue. In an example, a separate data processor can be in a wearable device (e.g. a smart watch), a mobile device (e.g. a cell phone), or a remote server (e.g. in a healthcare provider's server and/or cloud storage).

In an example, a cup on a smart bra can have three layers. The first layer is an interior layer which faces toward the surface of a person's breast. This interior layer can be elastic, stretchable, and flexible. In an example, this interior layer can also be transparent. If this interior layer is not transparent, then there can be holes in the interior layer through which optical components protrude for optical communication with breast tissue. The second layer is a middle layer. The middle layer contains the expandable components. In an example, the middle layer can be soft and compressible, with holes in which the expandable components are located. The third layer is the exterior layer. The exterior layer is less elastic, stretchable, or flexible than the first layer. The exterior layer can also be opaque to reduce penetration of light from the environment into the cup and/or reduce escape of light from the light emitters out of the cup.

In an example, a smart bra for spectroscopic scanning of breast tissue to help detect abnormal tissue can comprise: a smart bra with two cups which are configured to be worn on a person's breasts; wherein a cup has an internal layer which is closest to the surface of the person's breast, an external layer which is farthest from the surface of the person's breast, and a middle layer between the first internal layer and the external layer; wherein the internal layer is transparent and is made from a material with a first Shore 00 value; wherein the middle layer is compressible and contains a plurality of light emitters, light receivers, and electromagnetic actuators; wherein the exterior layer is opaque and is made from a material with a second Shore 00 value; and wherein the second Shore 00 value is greater than the Shore 00 value. In an example, the first Shore 00 value is less than 5 and the second Shore 00 value is greater than 5. In an example, the first Shore 00 value is less than 20 and the second Shore 00 value is greater than 20.

In an example, an optical component can comprise a light emitter which transmits light into breast tissue. In an example, an optical component can comprise a light receiver which receives light which has been transmitted through breast tissue (e.g. by reflection within breast tissue or by transmission into one side of the breast and out of another side of the breast). In an example, an optical component can comprise both a light emitter and a light receiver. In an example, an optical component can comprise one light emitter and a plurality of light receivers. In an example, an optical component can comprise one light emitter and a plurality of light receivers around the light emitter. In an example, an optical component can comprise one light receiver and a plurality of light emitters. In an example, an optical component can comprise one light receiver and a plurality of light emitters around the light receiver.

In an example, a light emitter can emit intensity or amplitude-modulated light. In an example, a light emitter can emit light with a frequency between 598 and 603 nm. In an example, a light emitter can emit light with a frequency between 978 and 983 nm. In an example, a light emitter can emit light with a frequency between 1208 and 1213 nm.

In an example, an array of optical components can be configured in nested and/or concentric rings on the cup of a smart bra. In an example, an array of optical components can be configured in radial spokes on the cup of a smart bra. In an example, an array of optical components can be configured in a spiral and/or helix on the cup of a smart bra. In an example, there can be a pattern of alternating light emitters and light receivers along a ring, radial spoke, spiral, or helix. In an example, light emitters can be clustered on one side (or quadrant) or a breast and light emitters can be clustered on the opposite side (or quadrant) of the breast, or vice versa. In an example, there can be between 5 and 20 optical components in a cup of a smart bra. In an example, there can be between 10 and 100 optical components in a cup of a smart bra. In an example, there can be more than 50 optical components in a cup of a smart bra.

In an example, a first light emitter can emit light with a wavelength in the range of 600 to 900 nm at a first time and a second light emitter can emit light with a wavelength in the range of 900 nm to 1200 nm at a second time. In an example, a first light emitter can emit light with a wavelength in the range of 600 to 900 nm at a first time; a second light emitter can emit light with a wavelength in the range of 900 nm to 1200 nm at a second time; and a third light emitter can emit light with a wavelength in the range of 1200 nm to 1500 nm at a third time.

In an example, angles between the focal vectors of light beams emitted from light emitters and the surface of a breast can vary with the distance of the light emitters from the apex of the concave surface of a breast. In an example, angles between the focal vectors of light emitted from light emitters and the surface of a breast can increase with the distance of the light emitters from the apex of the concave surface of a breast. In an example, the focal vectors of light emitted from light emitters which are farther from the apex of the concave surface of a breast can be closer to perpendicular to that surface than the focal vectors of light emitted from light emitters which are closer to the apex of the concave surface of the breast.

In an example, optical components can be on the interior surface of a cup. In an example, optical components can be in direct optical communication with the surface of a person's breast. In an example, optical components can be protected by a transparent layer which transmits light but protects the optical components from fluid intrusion when a smart bra is washed. Alternatively, optical components can be removably-attached to a smart bra (e.g. by a clip, clasp, or hook-and-eye material) so that they can be removed before the bra is washed. In an example, there can be an opaque layer between optical components and the exterior surface of a cup to isolate light receivers from ambient light and/or to prevent light from light emitters from shining out of the cup. In an example, an optical component can be attached to a cup by a gimbal mechanism which enables the component to tilt in order to better conform to a breast surface.

In an example, light from a light emitter which has been transmitted through breast tissue (by reflection or side-to-side transmission) and received by a light receiver can be spectroscopically analyzed to detect the presence, composition, shape, size, and/or location of abnormal breast tissue. In an example, changes in the spectral distribution of this light can be analyzed to detect the presence, composition, shape, size, and/or location of abnormal breast tissue. In an example, spectral changes of light transmitted between a plurality of pairs of light emitters and light receivers can be collectively analyzed (e.g. triangulated) in order to better identify the likely location of abnormal breast tissue.

In an example, a first light emitter on a cup can emit light with a wavelength in the range of 650 to 700 nm; a second light emitter on the cup can emit light with a wavelength in the range of 700 nm to 750 nm; and a third light emitter can emit light with a wavelength in the range of 750 nm to 800 nm. In an example, a light emitter can emit light energy with a wavelength in the range of 850 to 950 nm. In an example, a light emitter can emit light with a frequency between 778 and 783 nm. In an example, a light emitter can emit light with a frequency between 783 and 788 nm.

In an example: the surface of an optical component which faces toward the surface of a breast can be in a first virtual plane when the optical component is in the first configuration; the surface of the optical component which faces toward the surface of a breast can be in a second virtual plane when the optical component is in the second configuration; and the first and second virtual planes can be substantially parallel to each other. In an example: the surface of an optical component which faces toward the surface of a breast can be in a first virtual plane when the optical component is in the first configuration; the surface of the optical component which faces toward the surface of a breast can be in a second virtual plane when the optical component is in the second configuration; and the first and second virtual planes can intersect each other at an angle between 2 and 20 degrees.

In an example, the surface of an optical component which faces toward a breast can be substantially parallel with the interior surface of a cup in the first configuration. In an example, the surface of an optical component which faces toward a breast can protrude and/or extend out from the interior surface of the cup in the second configuration. In an example, the surface of an optical component which faces toward a breast can slide out from the interior surface of the cup in the second configuration. In an example, the surface of an optical component which faces toward a breast can locally stretch and/or distend a local portion the interior surface of the cup away from the rest of the interior surface in the second configuration. In an example, the interior surface of a cup can be non-undulating in the first configuration, but locally-undulating in the second configuration.

In an example, an expandable component can be located between an optical component and the exterior surface of a cup on a smart bra. In an example, the interior surface of a cup can be more elastic, stretchable, and/or compliant than the exterior surface of the cup, so that expansion of an expandable component between the interior and exterior surfaces extends the interior surface outward more than it extends the exterior surface outward. In an example, expansion of an expandable component pushes an optical component away from the interior surface of the cup toward the surface of a breast.

In an example, expansion of an expandable component pushes an optical component away from the interior surface of the cup toward the surface of a breast, thereby shrinking a gap between the optical component and the surface of the breast. In an example, expansion of an expandable component pushes an optical component away from the interior surface of the cup, thereby increasing the pressure level between the optical component and breast tissue. In an example, expansion of an expandable component pushes an optical component away from the interior surface of the cup toward the surface of a breast, thereby improving optical communication between the optical component and breast tissue.

In an example, an expandable component can be an electromagnetic actuator, motor, magnet, and/or solenoid. In an example, an expandable component can be an electromagnetic actuator, motor, magnet, and/or solenoid which is located between an optical component and the exterior surface of a cup on a smart bra. In an example, there can be an electromagnetic actuator for each optical component. In an example, electromagnetic actuators can be individually, selectively, and differentially activated so as to move selected optical components closer to a breast surface. This enables custom fitting of optical components to the particular shape of a specific breast to minimize optical scanning errors due to air gaps between optical components and the surface of the breast. In an example, a selected subset of electromagnetic actuators can be expanded in order to move a selected subset of optical components from their first to second configurations.

In an example, a smart bra can comprise an array of optical components (e.g. including a light emitter, light receiver, or both) and an array of electromagnetic actuators (e.g. electromagnetic motors, electromagnets, and/or or solenoids). In an example, optical components and electromagnetic actuators can be configured in pairs, wherein each pair has an optical component and an electromagnetic actuator. In an example, each electromagnetic actuator can independently and selectively change the configuration of an optical component in one or more ways selected from the group consisting of: changing the distance by which an optical component protrudes out from the interior surface of a bra cup; changing the distance between an optical component and the surface of a person's breast; closing an air gap between an optical component and the surface of a person's breast; changing the angle between an optical component and the interior surface of a bra cup; changing the angle between an optical component and the surface of a person's breast; changing the orientation of an optical component relative to the interior surface of a bra cup; and changing the orientation of an optical component relative to the surface of a person's breast.

In an example, an expandable component can have a longitudinal axis and an optical component can have a longitudinal axis, wherein these longitudinal axes are substantially parallel to each other. In an example, an expandable component can have a first width in the first configuration, wherein the first width is between 1 mm and 5 mm. In an example, an expandable component can have a second width in the second configuration, wherein the first width is between 2 mm and 10 mm. In an example, the second width can be greater than the first width. In an example, the second width can be at least 25% greater than the first width.

In an example, an expandable component can have a first cross-sectional area in a first plane which is parallel and/or tangential to the exterior surface of a cup. In an example, an optical component which is flexibly attached to the expandable component can have a second cross-sectional area in a second plane which is parallel and/or tangential to the exterior surface of a cup. In an example, the first cross-sectional area can be substantially the same size as (e.g. within 10% of) the second cross-sectional area. In an example, the first cross-sectional area can be larger than the second cross-sectional area. In an example, the first cross-sectional area can be at least 50% larger than the second cross-sectional area. In an example, the second cross-sectional area can be larger than the first cross-sectional area. In an example, the second cross-sectional area can be at least 50% larger than the first cross-sectional area.

In an example, an expandable component can be an electromagnetic actuator with a rotating helically-threaded cylinder. In an example, rotation of the threaded cylinder causes the cylinder to extend outward which, in turn, pushes a light emitter and/or light receiver outward from the interior layer of a cup. In an example, rotation of the threaded cylinder causes the cylinder to extend outward which, in turn, pushes a light emitter and/or light receiver toward the surface of a breast. In an example, an expandable component can be an electromagnet or solenoid. In an example, application of electrical energy to the electromagnet or solenoid causes a cylinder to extend outward which, in turn, pushes a light emitter and/or light receiver outward from the interior layer of a cup. In an example, application of electrical energy to the electromagnet or solenoid causes a cylinder to extend outward which, in turn, pushes a light emitter and/or light receiver toward the surface of a breast.

A smart bra which enables selective expansion of only a selected subset of expandable components (thereby moving only optical components which are not contacting breast surface) enables better optical scanning and comfort than a device that only enables uniform expansion. Selective expansion of a subset of expandable components closes gaps between optical components and a breast surface where there are gaps in a first configuration, without creating pressure or deformation between optical components and the breast surface where there are no gaps in the first configuration. This is an advantage over devices that only offer uniform expansion. A device that only offers uniform expansion can cause uncomfortable compression and/or pinching of areas of the breast where there are no air gaps when the device is uniformly expanded in an effort to close areas where there are air gaps.

In an example, the selection of which expandable components should be expanded can be based on which optical components have errors in optical scanning data, wherein these errors indicate air gaps between the optical components and surface of a breast. In an example, the selection of which expandable components should be expanded by the device can be based on infrared light reflection. In an example, a smart bra can further comprise an array of pressure sensors. In an example, the selection of which expandable components should be expanded by the device can be based on which optical components are near pressure sensors which indicate no contact with the breast surface.

In an example, a smart bra for spectroscopic scanning of breast tissue to help detect abnormal tissue can comprise: a bra with two cups which is configured to be worn on a person's breasts, wherein an interior surface of a cup faces toward the person's breast and an exterior surface of the cup faces away from the person's breast; and an array of optical components on the interior surface of a cup; wherein each optical component further comprises: a light emitter which transmits light into the person's breast and/or a light receiver which receives light which has been transmitted (e.g. reflected or side-to-side transmitted) through the person's breast, and an electromagnetic actuator which pushes the light emitter and/or light receiver toward the surface of the person's breast when the electromagnetic actuator is activated. In an example, activation of electromagnetic actuators closes gaps between light emitters and/or light receivers and the surface of the person's breast.

In an example, a smart bra for spectroscopic scanning of breast tissue to help detect abnormal tissue can comprise: a bra with two cups which is configured to be worn on a person's breasts, wherein an interior surface of a cup faces toward the person's breast and an exterior surface of the cup faces away from the person's breast; and an array of optical components on the interior surface of a cup; wherein each optical component further comprises a light emitter which transmits light into the person's breast and an electromagnetic actuator which pushes the light emitter toward the surface of the person's breast when the electromagnetic actuator is activated. In an example, optical components for which there are air gaps between a light emitter and the surface of the person's breast can be detected by spectroscopic analysis of light which has been transmitted (e.g. reflected or side-to-side transmitted) from the light emitter through breast tissue. For optical components for which such air gaps are detected, electromagnetic actuators in those components are activated until spectroscopic analysis shows that the gaps have been closed.

In an example, a smart bra for spectroscopic scanning of breast tissue to help detect abnormal tissue can comprise: (i) a bra with two cups which is configured to be worn on a person's breasts, wherein an interior surface of a cup faces toward the person's breast and an exterior surface of the cup faces away from the person's breast; (ii) an array of optical components on the interior surface of a cup, wherein each optical component further comprises a light emitter which transmits light into the person's breast and/or a light receiver which receives light which has been transmitted (e.g. reflected or side-to-side transmitted) through breast tissue; and (iii) an array of electromagnetic actuators, wherein the electromagnetic actuators selectively change the configurations of one or more optical components in the array of optical components in one or more ways selected from the group consisting of: changing the distances by which one or more optical components protrude out from the interior surface of a bra cup; changing the distances between one or more optical components and the surface of a person's breast; closing air gaps between one or more optical components and the surface of a person's breast; changing the angles between one or more optical components and the interior surface of a bra cup; changing the angles between one or more optical components and the surface of a person's breast; changing the orientations of one or more optical components relative to the interior surface of a bra cup; and changing the orientations of one or more optical components relative to the surface of a person's breast.

In an example, a smart bra for spectroscopic scanning of breast tissue to help detect abnormal tissue can comprise: (i) a bra with two cups which is configured to be worn on a person's breasts, wherein an interior surface of a cup faces toward the person's breast, and wherein an exterior surface of the cup faces away from the person's breast; (ii) a first optical component on the interior surface of a cup, wherein the first optical component comprises a light emitter which transmits light into the person's breast and/or a light receiver which receives light which has been transmitted (e.g. reflected or side-to-side transmitted) through the person's breast; (iii) a first electromagnetic actuator, wherein activation of the first electromagnetic actuator moves the first optical component; (iv) a second optical component on the interior surface of a cup, wherein the second optical component comprises a light emitter which transmits light into the person's breast and/or a light receiver which receives light which has been transmitted (e.g. reflected or side-to-side transmitted) through the person's breast; and (v) a second electromagnetic actuator, wherein activation of the second electromagnetic actuator moves the second optical component, and wherein the first electromagnetic actuator and the second electromagnetic actuator can be activated independently from each other. Relevant variations discussed elsewhere in this disclosure or in priority-linked disclosures can also be applied to these figures and examples.

FIGS. 5 and 6 show views, at two different times, of a smart bra for spectroscopic scanning of breast tissue to help detect abnormal tissue. This embodiment has piezoelectric elements which help shape the bra to the contour of a breast for more accurate optical scanning FIG. 5 shows this smart bra at a first time, before it has been adjusted to close any air gaps between optical scanning components and the surface of a breast. FIG. 6 shows this smart bra at a second time, after it has been adjusted to close any air gaps between optical scanning components and the surfaces of the breast. The upper portions of FIGS. 5 and 6 show opaque frontal views of the smart bra. Dotted-line ellipses in the lower portions of FIGS. 5 and 6 show cross-sectional close-up views of optical components, piezoelectric components, a lower portion of the breast, and air gaps between some of the optical components and the surface of the breast. These air gaps are closed by the device in FIG. 6.

The smart bra shown in FIGS. 5 and 6 can be described as a smart bra for spectroscopic scanning of breast tissue to help detect abnormal tissue which comprises: (i) a bra with two cups which is configured to be worn on a person's breasts, wherein an interior surface of a cup faces toward the person's breast and an exterior surface of the cup faces away from the person's breast; (ii) a first optical component on the interior surface of a cup, wherein the first optical component comprises a light emitter which transmits light into the person's breast and/or a light receiver which receives light which has been transmitted (e.g. reflected or side-to-side transmitted) through the person's breast, wherein the first optical component is a first distance from the surface of the person's breast in a first configuration and a second distance from the surface of the person's breast in a second configuration, and wherein a first distance adjustment is the first distance minus the second distance; (iii) a first piezoelectric component attached to the first optical component, wherein contraction of the first piezoelectric component moves the first optical component from the first configuration to the second configuration; (iv) a second optical component on the interior surface of the cup, wherein the second optical component comprises a light emitter which transmits light into the person's breast and/or a light receiver which receives light which has been transmitted (e.g. reflected or side-to-side transmitted) through the person's breast, wherein the second optical component is a third distance from the surface of the person's breast in the first configuration and a fourth distance from the surface of the person's breast in the second configuration, wherein a second distance adjustment is the third distance minus the fourth distance, and wherein the second distance adjustment is greater than the first distance adjustment; and (v) a second piezoelectric component attached to the second optical component, wherein contraction of the second piezoelectric component moves the second optical component from the first configuration to the second configuration.

With respect to specific components, the smart bra shown in FIGS. 5 and 6 comprises: (i) a bra 501 with two cups which is configured to be worn on a person's breasts, wherein an interior surface of a cup faces toward the person's breast 510, and wherein an exterior surface of the cup faces away from the person's breast; (ii) a first optical component on the interior surface of a cup, wherein the first optical component comprises a light emitter 507 which transmits light into the person's breast and a light receiver 508 which receives light which has been transmitted (e.g. reflected or side-to-side transmitted) through the person's breast, wherein the first optical component is a first distance from the surface of the person's breast in a first configuration (shown in FIG. 5) and a second distance from the surface of the person's breast in a second configuration (shown in FIG. 6), and wherein a first distance adjustment is the first distance minus the second distance; (iii) a first piezoelectric component 506 attached to the first optical component, wherein contraction of the first piezoelectric component moves the first optical component from the first configuration to the second configuration; (iv) a second optical component on the interior surface of the cup, wherein the second optical component comprises a light emitter 503 which transmits light into the person's breast and a light receiver 504 which receives light which has been transmitted (e.g. reflected or side-to-side transmitted) through the person's breast, wherein the second optical component is a third distance from the surface of the person's breast in the first configuration (shown in FIG. 5) and a fourth distance from the surface of the person's breast in the second configuration (shown in FIG. 6), wherein a second distance adjustment is the third distance minus the fourth distance, and wherein the second distance adjustment is greater than the first distance adjustment; and (v) a second piezoelectric component 505 attached to the second optical component, wherein contraction of the second piezoelectric component moves the second optical component from the first configuration to the second configuration. FIGS. 5 and 6 also show additional piezoelectric components 509 and 502 which also span between optical components.

Application of electromagnetic energy to a piezoelectric component causes the component to shrink. This shrinks a portion of a cup, drawing a portion of the interior surface of the cup and a subset of optical components closer to the surface of the breast. This closes air gaps and reduces errors in optical scanning of the breast. In FIG. 5, a first optical component (including light emitter 507 and light receiver 508) has close contact with the surface of breast tissue 510, but there is an air gap between a second optical component (including light emitter 503 and light receiver 504) and breast tissue. This air gap can cause errors in optical scanning of breast tissue. In FIG. 6, a second piezoelectric component 505 has been contracted by the device, thereby drawing the second optical component closer to the surface of the breast tissue. This closes the air gap and reduced errors in optical scanning. Differential contraction of the second piezoelectric component relative to the first piezoelectric component helps the smart bra to better conform to the shape of the breast, reducing air gaps and improving the quality of optical scanning, without expanding other areas of the cup which could cause tightness or discomfort.

In an example, a piezoelectric component can shrink when electromagnetic current is transmitted into it. In an example, a piezoelectric component can be a longitudinal strip or band of material whose length shrinks when electromagnetic current is transmitted through it. In an example, a smart bra can be made and sold in standard bra sizes (e.g. standard chest and cup sizes). In an example, a smart bra can be made with a stretchable, elastic, flexible, and/or conforming material (e.g. stretchable, elastic, flexible, and/or conforming fabric). In an example, a smart bra can have optical components on both cups in order to optically scan both breasts. In an example, results from optical scanning of right and left breasts can be compared and/or contrasted to help detect abnormal breast tissue. Also, results from more recent scans can be compared and/or contrasted with earlier scans to help detect growth of abnormal breast tissue.

In an example, an optical component can further comprise one or more components selected from the group consisting of: a mirror; a micromirror array; a lens; an optical filter, and a prism. In an example, a smart bra can comprise additional electronic and mechanical components which are located on the back strap of the bra. These additional electronic and mechanical components can be selected from the group consisting of: a battery; a data processor; a memory; a wireless data transmitter; and a wireless data receiver.

In an example, a smart bra can be worn on a periodic (e.g. annual, monthly, weekly, or daily) basis in order to obtain a periodic longitudinal time series of optical of breast tissue for identification of possible changes in tissue composition. In an example, a smart bra can be worn as a regular undergarment during everyday life for relatively-continuous monitoring for early identification of possible changes in tissue composition. In an example, data from light receivers in a smart bra can be transmitted to a separate data processor for spectroscopic analysis to identify changes in breast tissue composition and/or help identify abnormal breast tissue. In an example, a separate data processor can be in a wearable device (e.g. a smart watch), a mobile device (e.g. a cell phone), or a remote server (e.g. in a healthcare provider's server and/or cloud storage).

In an example, a cup on a smart bra can have three layers. The first layer is an interior layer which faces toward the surface of a person's breast. This interior layer can be elastic, stretchable, and flexible. In an example, this interior layer can also be transparent. If this interior layer is not transparent, then there can be holes in the interior layer through which optical components protrude for optical communication with breast tissue. The second layer is a middle layer. The middle layer contains piezoelectric components. The third layer is the exterior layer. The exterior layer can also be opaque to reduce penetration of light from the environment into the cup and/or reduce escape of light from the light emitters out of the cup.

In an example, an optical component can comprise a light emitter which transmits light into breast tissue. In an example, an optical component can comprise a light receiver which receives light which has been transmitted through breast tissue (e.g. by reflection within breast tissue or by transmission into one side of the breast and out of another side of the breast). In an example, an optical component can comprise both a light emitter and a light receiver. In an example, an optical component can comprise one light emitter and a plurality of light receivers. In an example, an optical component can comprise one light emitter and a plurality of light receivers around the light emitter. In an example, an optical component can comprise one light receiver and a plurality of light emitters. In an example, an optical component can comprise one light receiver and a plurality of light emitters around the light receiver.

In an example, a first light emitter on a cup can emit light with a wavelength in the range of 600 to 900 nm; a second light emitter on the cup can emit light with a wavelength in the range of 900 nm to 1200 nm; and a third light emitter can emit light with a wavelength in the range of 1200 nm to 1500 nm. In an example, a first light emitter can emit light with a wavelength in the range of 650 to 750 nm; a second light emitter on the (base) perimeter of the cup can emit light with a wavelength in the range of 750 nm to 850 nm; and a third light emitter can emit light with a wavelength in the range of 850 nm to 950 nm.

In an example, angles between the focal vectors of light beams emitted from light emitters and the surface of a breast can vary with the distance of the light emitters from the apex of the concave surface of a breast. In an example, angles between the focal vectors of light emitted from light emitters and the surface of a breast can increase with the distance of the light emitters from the apex of the concave surface of a breast. In an example, the focal vectors of light emitted from light emitters which are farther from the apex of the concave surface of a breast can be closer to perpendicular to that surface than the focal vectors of light emitted from light emitters which are closer to the apex of the concave surface of the breast.

In an example, optical components can be on the interior surface of a cup. In an example, optical components can be in direct optical communication with the surface of a person's breast. In an example, optical components can be protected by a transparent layer which transmits light but protects the optical components from fluid intrusion when a smart bra is washed. Alternatively, optical components can be removably-attached to a smart bra (e.g. by a clip, clasp, or hook-and-eye material) so that they can be removed before the bra is washed. In an example, there can be an opaque layer between optical components and the exterior surface of a cup to isolate light receivers from ambient light and/or to prevent light from light emitters from shining out of the cup. In an example, an optical component can be attached to a cup by a gimbal mechanism which enables the component to tilt in order to better conform to a breast surface.

In an example, light from a light emitter which has been transmitted through breast tissue (by reflection or side-to-side transmission) and received by a light receiver can be spectroscopically analyzed to detect the presence, composition, shape, size, and/or location of abnormal breast tissue. In an example, changes in the spectral distribution of this light can be analyzed to detect the presence, composition, shape, size, and/or location of abnormal breast tissue. In an example, spectral changes of light transmitted between a plurality of pairs of light emitters and light receivers can be collectively analyzed (e.g. triangulated) in order to better identify the likely location of abnormal breast tissue.

In an example, a first light emitter can emit light with a wavelength in the range of 600 to 700 nm at a first time; a second light emitter can emit light with a wavelength in the range of 700 nm to 800 nm at a second time; and a third light emitter can emit light with a wavelength in the range of 800 nm to 900 nm at a third time. In an example, a light emitter can emit light with a frequency between 798 and 803 nm. In an example, a light emitter can emit light with a frequency between 658 and 663 nm. In an example, a light emitter can emit light with a frequency between 806 and 811 nm. In an example, a light emitter can emit light with a frequency between 825 and 830 nm.

In an example: the surface of an optical component which faces toward the surface of a breast can be in a first virtual plane when the optical component is in the first configuration; the surface of the optical component which faces toward the surface of a breast can be in a second virtual plane when the optical component is in the second configuration; and the first and second virtual planes can be substantially parallel to each other. In an example: the surface of an optical component which faces toward the surface of a breast can be in a first virtual plane when the optical component is in the first configuration; the surface of the optical component which faces toward the surface of a breast can be in a second virtual plane when the optical component is in the second configuration; and the first and second virtual planes can intersect each other at an angle between 2 and 20 degrees. Relevant variations discussed elsewhere in this disclosure or in priority-linked disclosures can also be applied to these figures and examples.

FIGS. 7 and 8 show close-up cross-sectional views, at two different times, of a lower section of a smart bra for spectroscopic scanning of breast tissue. FIG. 7 shows this section at a first time, before the fit of the bra has been adjusted to close air gaps between optical scanning components and the surface of a breast. FIG. 8 shows this section at a second time, after the fit of the bra has been adjusted to close air gaps between optical scanning components and the surface of the breast. These close-up views show optical components, expandable components, a lower a portion of the breast, and an air gap between one of the optical components and the surface of the breast. This air gap is open in FIG. 7, but closed by the device in FIG. 8.

The section of a smart bra shown in FIGS. 7 and 8 is a section of a smart bra for spectroscopic scanning of breast tissue which comprises: (i) a bra with two cups which is configured to be worn on a person's breasts, wherein an interior surface of a cup faces toward the person's breast and an exterior surface of the cup faces away from the person's breast; (ii) a first optical component on the interior surface of the cup, wherein the first optical component comprises a light emitter which transmits light into the person's breast and/or a light receiver which receives light which has been transmitted (e.g. reflected or side-to-side transmitted) through the person's breast, wherein the first optical component is a first distance from the surface of the person's breast in a first configuration and a second distance from the surface of the person's breast in a second configuration, and wherein a first distance adjustment is the first distance minus the second distance; (iii) a first expandable component, wherein expansion of the first expandable component moves the first optical component from the first configuration to the second configuration; (iv) a second optical component on the interior surface of the cup, wherein the second optical component comprises a light emitter which transmits light into the person's breast and/or a light receiver which receives light which has been transmitted (e.g. reflected or side-to-side transmitted) through the person's breast, wherein the second optical component is a third distance from the surface of the person's breast in the first configuration and a fourth distance from the surface of the person's breast in the second configuration, wherein a second distance adjustment is the third distance minus the fourth distance, and wherein the second distance adjustment is greater than the first distance adjustment; and (v) a second expandable component, wherein expansion of the second expandable component moves the second optical component from the first configuration to the second configuration. This section is compatible with the smart bra examples shown in FIGS. 1 through 4.

With respect to specific components, the section of a smart bra shown in FIGS. 7 and 8 comprises: (i) a first optical component, wherein the first optical component comprises a light emitter 706 which transmits light into the person's breast 701 and a light receiver 708 which receives light which has been transmitted (e.g. reflected or side-to-side transmitted) through the person's breast, wherein the first optical component is a first distance from the surface of the person's breast in a first configuration (shown in FIG. 7) and a second distance from the surface of the person's breast in a second configuration (shown in FIG. 8), and wherein a first distance adjustment is the first distance minus the second distance; (ii) a first expandable component 707, wherein expansion of the first expandable component moves the first optical component from the first configuration to the second configuration; (iii) a second optical component on the interior surface of the cup, wherein the second optical component comprises a light emitter 702 which transmits light into the person's breast and a light receiver 704 which receives light which has been transmitted (e.g. reflected or side-to-side transmitted) through the person's breast, wherein the second optical component is a third distance from the surface of the person's breast in the first configuration (shown in FIG. 7) and a fourth distance from the surface of the person's breast in the second configuration (shown in FIG. 8), wherein a second distance adjustment is the third distance minus the fourth distance, and wherein the second distance adjustment is greater than the first distance adjustment; and (iv) a second expandable component 703, wherein expansion of the second expandable component moves the second optical component from the first configuration to the second configuration.

The section of a smart bra which is shown in FIGS. 7 and 8 further comprises a tube or channel 705 into one or more of the expandable components. In the example shown in FIGS. 7 and 8, expandable components 703 and 707 are fluid bladders which can be expanded by inflation with a gas (e.g. air) or infilling with a liquid (e.g. water). FIG. 8 shows the path 801 of a flowable substance delivered through the tube or channel into expandable component 703, which causes the expandable component to expand, which pushes the optical component toward the surface of the breast, which closes the air gap for better optical scanning of breast tissue.

FIGS. 7 and 8 also show additional detail concerning the layers of the smart bra section (e.g. the layers of a cup on the smart bra). FIGS. 7 and 8 show that the smart bra cup has an interior layer 711 which faces toward the surface of the breast, an exterior layer 709 which faces away from the surface of the breast, and a middle layer 710 between the interior layer and the exterior layer. In an example, the interior layer can be elastic and transparent. In an example, the middle layer can be compressible. In an example, the exterior layer can be opaque.

In this example, the optical components and expandable components are between the interior layer and the exterior layer. In this example, the optical components and expandable components are in holes or openings in the middle layer. In this example, the transparent interior layer allows the optical components to be in optical communication with breast tissue, while also protecting the optical components from moisture when the bra is washed. In this example, the interior layer is folded and/or elastic so that it can unfold and/or stretch outward toward to close an air gap when an expandable component is expanded. In this example, the interior layer is folded and/or undulated (on both sides of the optical component and the expandable component) when the expandable component is not expanded. In this example, the interior layer unfolds and or changes shape (e.g. shifts the direction of undulation) to partially protrude out from the cup toward the breast surface when the expandable component is expanded. In an example, a local area of an interior layer over an optical component can change from being concave to being convex when the optical component is changed from its first configuration to its second configuration.

In an example, the interior layer of a cup on a smart bra can be the most elastic, most transparent, and thinnest layer of the cup. In an example, the interior layer can be made with PDMS or another silicone-based polymer. In an example, the interior layer can be between 0.5 mm and 2 mm thick. In an example, the middle layer of the cup can be the thickest layer of the cup. In an example, the interior layer can be between 2 mm and 8 mm thick. In an example, the exterior layer of the cup can be the least elastic and most opaque layer of the cup. In an example, the exterior layer can be between 1 mm and 5 mm thick.

In an example, an expandable component can have a pleated configuration, like an accordion or bellows. This can enable the expandable component to expand further and/or change shape as it expanded. For example, in FIG. 8, the breast-facing side of the expandable component not only moves away from the exterior layer, but the angle of the breast-facing side of the expandable component relative to the exterior layer changes as the expandable component is expanded in order to better conform the optical component to the contour of the surface of the breast.

In FIGS. 7 and 8, only one tube or channel is shown and it is connected to both of the expandable components. In an example, there can be multiple tubes or channels, one for each expandable component, enabling more selective expansion of individual expandable components and/or sets of expandable components. This can enable closing air gaps between optical components and the surface of a breast without causing tightness and/or discomfort in other areas of a cup where there are no air gaps. In another example, expandable components can be electromagnetic actuators which are expanded by transmission of electromagnetic energy through wires or conductive fibers, instead of by transmission of a flowable substance through a tube or channel Relevant variations discussed elsewhere in this disclosure or in priority-linked disclosures can also be applied to these figures and examples.

In an example, a smart bra for optical scanning of breast tissue can comprise: (i) a bra with two cups which is configured to be worn on a person's breasts, wherein an interior surface of a cup faces toward the person's breast and an exterior surface of the cup faces away from the person's breast; (ii) a first optical component on the interior surface of the cup, wherein the first optical component comprises a light emitter which transmits light into the person's breast and/or a light receiver which receives light which has been transmitted through the person's breast, wherein the first optical component is a first distance from the surface of the person's breast in a first configuration and a second distance from the surface of the person's breast in a second configuration, and wherein a first distance adjustment is the first distance minus the second distance; (iii) a first expandable component, wherein expansion of the first expandable component moves the first optical component from the first configuration to the second configuration; (iv) a second optical component on the interior surface of the cup, wherein the second optical component comprises a light emitter which transmits light into the person's breast and/or a light receiver which receives light which has been transmitted through the person's breast, wherein the second optical component is a third distance from the surface of the person's breast in the first configuration and a fourth distance from the surface of the person's breast in the second configuration, wherein a second distance adjustment is the third distance minus the fourth distance, and wherein the second distance adjustment is greater than the first distance adjustment; and (v) a second expandable component, wherein expansion of the second expandable component moves the second optical component from the first configuration to the second configuration.

In an example, an expandable component can be a bladder which is expanded by being filled with a gas or liquid and the smart bra can have a plurality of tubes or channels through which the gas or liquid is delivered into expandable components. In an example, there can be different tubes or channels for different expandable components so that a selected subset of expandable components can be expanded. Alternatively, an expandable component can be an electromagnetic actuator and the smart bra can have a plurality of wires or electroconductive fibers through which electricity is delivered to expandable components. In an example, there can be different wires or electroconductive fibers for different expandable components so that a selected subset of expandable components can be expanded.

In an example, there can be an elastic transparent layer between optical components and the surface of the person's breast. In an example, a cup of a smart bra can have an interior layer which faces toward the surface of the person's breast, an exterior layer which faces away from the surface of the person's breast, and a middle layer between the interior layer and the exterior layer. In an example, optical components and expandable components can be in the middle layer. In an example, the interior layer can be more transparent than the exterior layer. In an example, the interior layer can be more elastic than the exterior layer. Relevant variations discussed elsewhere in this disclosure or in priority-linked disclosures can also be applied to these examples.

I claim:

1. A smart bra for optical scanning of breast tissue comprising:
    a bra with a first cup and a second cup which are configured to be worn on a person's first breast and second breast, respectively, wherein an interior surface of the first cup faces toward the first breast and an exterior surface of the first cup faces away from the first breast;
    a first optical component on the interior surface of the first cup, wherein the first optical component comprises a first light emitter which is configured to transmit light into the first breast and/or a first light receiver which is configured to receive light which has been transmitted through the first breast, wherein the first optical component is a first distance from the surface of the first breast in a first configuration and a second distance from the surface of the first breast in a second configuration, wherein a first distance adjustment is the first distance minus the second distance, and wherein the first optical component is a third distance from an apex of the concave surface of the first breast;
    a first fluid-filled bladder, the first fluid-filled bladder being configured to expand by being filled with a gas or a liquid, thereby moving the first optical component from the first configuration to the second configuration;
    a second optical component on the interior surface of the first cup, wherein the second optical component comprises a second light emitter which is configured to transmit light into the first breast and/or a second light receiver which is configured to receive light which has been transmitted through the first breast, wherein the second optical component is a fourth distance from the surface of the first breast in the first configuration and a fifth distance from the surface of the first breast in the second configuration, wherein a second distance adjustment is the fourth distance minus the fifth distance, and wherein the second distance adjustment is greater than the first distance adjustment, wherein the second optical component is a sixth distance from the apex of the concave surface of the first breast, wherein the sixth distance is greater than the third distance, and wherein a focal vector of the second light emitter is closer to being perpendicular to the surface of the first breast than a focal vector of the first light emitter; and
    a second fluid-filled bladder, the second fluid-filled bladder being configured to expand by being filled with the gas or the liquid, thereby moving the second optical component from the first configuration to the second configuration.

2. The smart bra in claim 1 wherein there are different tubes or channels for delivering the gas or the liquid to the first fluid-filled bladder and to the second fluid-filled bladder.

3. The smart bra in claim 1 wherein there is an elastic transparent layer between: the first optical component and the second optical component; and the surface of the person's breast.

4. The smart bra in claim 1: wherein the cup has an interior layer which faces toward the surface of the person's breast, an exterior layer which faces away from the surface of the person's breast, and a middle layer between the interior layer and the exterior layer.

5. The smart bra in claim 4 wherein the first fluid-filled bladder and the second fluid-filled bladder are in the middle layer.

6. The smart bra in claim 4 wherein the interior layer is more transparent than the exterior layer.

7. The smart bra in claim 4 wherein the interior layer is more elastic than the exterior layer.

* * * * *